United States Patent [19]

Tada et al.

[11] Patent Number: 4,946,951

[45] Date of Patent: Aug. 7, 1990

[54] 2'-DEOXY-5-FLUOROURIDINE DERIVATIVES

[75] Inventors: Yukio Tada; Atsuhiko Uemura; Mitsugi Yasumoto, all of Honjyo; Setsuo Takeda, Tokushima; Hitoshi Saito, Tokushima; Norio Unemi, Tokushima, all of Japan

[73] Assignee: Taiho Pharmaceutical Co., Ltd., Tokyo, Japan

[21] Appl. No.: 225,984

[22] Filed: Jul. 29, 1988

[30] Foreign Application Priority Data

Jul. 31, 1987 [JP] Japan ................... 62-193192

[51] Int. Cl.$^5$ .................. C07H 19/073; A61K 31/70
[52] U.S. Cl. ...................................... 536/23
[58] Field of Search ................ 536/23; 514/274, 269, 514/49, 50

[56] References Cited

U.S. PATENT DOCUMENTS

| | | | |
|---|---|---|---|
| 4,340,728 | 7/1982 | Endo et al. | 536/23 |
| 4,599,404 | 7/1988 | Fujii et al. | 536/23 |
| 4,605,645 | 8/1986 | Watanabe et al. | 514/51 |
| 4,757,139 | 7/1988 | Kawaguchi et al. | 536/23 |

FOREIGN PATENT DOCUMENTS

| | | |
|---|---|---|
| 0180897 | 5/1986 | European Pat. Off. . |
| 0129984 | 3/1988 | European Pat. Off. . |
| 2658672 | 6/1978 | Fed. Rep. of Germany . |
| 57-91996 | 6/1982 | Japan . |
| 57-91997 | 6/1982 | Japan . |
| 57-91998 | 6/1982 | Japan . |
| 59-29699 | 2/1984 | Japan . |
| 61-189292 | 8/1986 | Japan . |
| 62-187484 | 8/1987 | Japan . |

Primary Examiner—Johnnie R. Brown
Assistant Examiner—Gary L. Kunz
Attorney, Agent, or Firm—Armstrong, Nikaido, Marmelstein, Kubovcik & Murray

[57] ABSTRACT

Disclosed is a 2'-deoxy-5-fluorouridine derivative of the formula

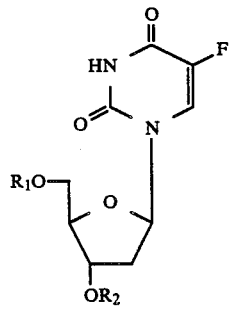

(I)

wherein one of $R_1$ and $R_2$ is a benzyl group which may optionally have substituent selected from the group consisting of $C_1$–$C_6$ alkyl group, $C_1$–$C_6$ alkoxy group, $C_1$–$C_3$ halogenated alkyl group, halogen atom, hydroxyl group and nitro group on the phenyl ring, and the other constitutes an amino acid residue, or a salt thereof. The compounds are useful for treating cancer.

22 Claims, No Drawings

2'-DEOXY-5-FLUOROURIDINE DERIVATIVES

BACKGROUND OF THE INVENTION

This invention relates to novel 2'-deoxy-5-fluorouridine derivatives and salts thereof. These compounds have a high anti-cancer activity and an excellent antiviral activity, and are useful as antitumor agents or as antiviral agents.

2'-Deoxy-5-fluorouridine (FudR) exhibits a high antitumor activity but has a high toxicity, posing a problem of being limited in safety margin.

Various 2'-deoxy-5-fluorouridine derivatives have been developed to overcome this problem. For example, Japanese Unexamined Patent Publications Nos.61,591/1985 and 106,593/1985 disclose numerous 2'-deoxy-5-fluorouridine derivatives. The disclosed 2'-deoxy-5-fluorouridine derivatives have moderated the problem to a certain extent but are not satisfactorily high in antitumor activity and are insufficient in therapeutic index, absorption and the like.

We conducted extensive research to overcome the foregoing prior art problem and successfully developed novel 2'-deoxy-5-fluorouridine derivatives which are higher in antitumor activity than conventional 2'-deoxy-5-fluorouridine derivatives and which are highly safe to human body. The present invention has been accomplished based on this novel finding.

SHORT STATEMENT OF THE INVENTION

This invention provides a 2'-deoxy-5-fluorouridine derivative represented by the formula (I)

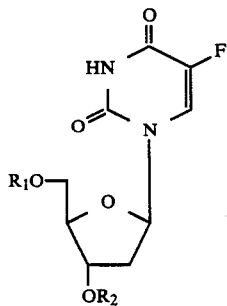

(I)

wherein:
one of $R_1$ and $R_2$ is a benzyl group which may optionally have substituent selected from the group consisting of $C_1$–$C_6$ alkyl group, $C_1$–$C_6$ alkoxy group, halogenated $C_1$–$C_3$ alkyl group, halogen atom, hydroxyl group and nitro group on the phenyl ring, and the other constitutes an amino acid residue.

The compounds of the formula (I) according to this invention are characterized in that the compounds are useful as antitumor agents and antiviral agents, low in toxicity readily soluble in water and wide in safety margin.

DETAILED DESCRIPTION OF THE PREFERRED EMBODIMENT

Given below are specific examples of substituents in the benzyl group represented by $R_1$ and $R_2$ in the formula (I).

Examples of the alkyl group as the substituent for the benzyl group are straight- or branched-chain alkyl groups having 1 to 6 carbon atoms such as methyl, ethyl, propyl, isopropyl, butyl, sec-butyl, tert-butyl, pentyl, hexyl and the like.

Examples of the alkoxy group as the substituent are straight- or branched-chain alkoxy groups having 1 to 6 carbon atoms such as methoxy, ethoxy, propoxy, isopropoxy, butoxy, sec-butoxy, tert-butoxy, pentyloxy, hexyloxy and the like.

Examples of the halogen atom as the substituent are fluorine, chlorine, bromine, iodine and the like.

Examples of the halogenated alkyl group as the substituent are alkyl groups each having 1 to 3 carbon atoms and substituted with 1 to 3 halogen atoms, such as chloromethyl, bromomethyl, trifluoromethyl, 1,2-dichloroethyl, 1,2-difluoroethyl, 2,2,2-trifluoroethyl and the like.

The number of substituents on the benzyl group, as represented by $R_1$ or $R_2$, is preferably 1, 2 or 3.

Preferred examples of the benzyl group optionally having 1 to 3 substituents are benzyl and a benzyl group having 1 or 2 substituents on the phenyl ring, such as 2-chlorobenzyl, 3-chlorobenzyl, 4-chlorobenzyl, 2-bromobenzyl, 3-bromobenzyl, 4-bromobenzyl, 2-fluorobenzyl, 3-fluorobenzyl, 4-fluorobenzyl, 2,4-dichlorobenzyl, 3,4-dichlorobenzyl, 2-chloro-4-bromobenzyl, 2-trifluoromethylbenzyl, 4-trifluoromethylbenzyl, 4-nitrobenzyl, 2,4-dinitrobenzyl, 2-methylbenzyl, 4-methylbenzyl, 4-ethylbenzyl, 4-tert-butylbenzyl, 4-methoxybenzyl, 3-ethoxybenzyl, 4-hydroxybenzyl, 2,4dihydroxybenzyl, 2-methyl-3-nitrobenzyl and the like.

Generally, benzyl groups having 1 or 2 halogen atoms on the phenyl ring are more preferred.

The term "amino acid residue" used herein refers to the monovalent group remaining after the removal of the OH group from the carboxyl group of amino acid. The term "amino acid" used herein is intended to include natural amino acids and synthetic amino acids which are compounds each containing at least one amino group and at least one carboxyl group and each having 2 to 20 carbon atoms in the molecule.

Examples of natural amino acids are those which are organisms' protein constituents, such as alanine, isoleucine, glycine, serine, threonine, valine, leucine, arginine, lysine, asparagine, aspartic acid, glutamine, glutamic acid, cystine, cysteine, methionine, tyrosine, phenylalanine, tryptophan, histidine, hydroxyproline, proline, etc. Natural amino acids and synthetic amino acids which are not organisms' protein constituents but play an important role in the living organism are also included, and examples thereof are sarcosine, creatine, homocystine, cysteinesulfonic acid, norleucine, isoserine, homoserine, hydroxylysine, norvaline, dehydrovaline, ornithine, arginosuccinic acid, dopa, 3-monoiodotyrosine, 3,5-diiodotyronine, thyroxine, $\alpha,\gamma$-diaminobutyric acid, 2,3-diaminosuccinic acid, $\alpha$-aminoadipic acid, $\alpha,\beta$-diaminopropionic acid, saccharopine, $\beta$-alanine, $\gamma$-aminobutyric acid, $\beta$-aminobutyric acid, $\epsilon$-aminocaproic acid, acediasulfone, agaristine, aranocine, hadacidin, melphalan, ibotenic acid and the like. Further examples are acetylserine, acetylthreonine, benzylaspartic acid and the like, namely substituted amino acids having acetyl group, ethoxycarbonyl group, benzyloxycarbonyl group or benzyl group as a substituent for hydroxyl group, amino group or carboxyl group of amino acids such as serine, threonine and like hydroxyamino acids, asparagine, ornithine, lysine and like basic amino acids having at least two amino groups, glutamic acid, aspartic acid and like acidic amino acids having at least two carboxyl groups.

An α-amino acid residue is preferred among amino acid residues represented by $R_1$ or $R_2$ in the compounds of the present invention More preferred are amino acid residues as protein constituents. Specific examples of such amino acid residues are the residues of alanine, isoleucine, glycine, serine, threonine, valine, leucine, arginine, hydroxylysine, lysine, asparagine, aspartic acid, glutamine, glutamic acid, cystine, cysteine, methionine, tyrosine, phenylalanine, tryptophan, histidine, hydroxyproline, proline and the like. Most preferred are the residues of alanine, isoleucine, glycine, O-acetylserine, valine, leucine, lysine, aspartic acid-β-benzyl ester, phenylalanine, histidine, proline and the like.

The amino acid residues according to the present invention may include those represented by the formula

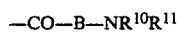 (f)

wherein B is a lower alkylene group which may optionally have phenyl or lower alkylthio group, and $R^{10}$ and $R^{11}$ each represent a hydrogen atom or lower alkyl group, or taken together with the nitrogen atom to which they are attached and form piperidine ring, and the amino acid residues also include a pyrrolidinylcarbonyl or piperidylcarbonyl group in which the carbonyl group is not attached to the nitrogen atom in the hetero ring.

With respect to the amino acid residue of the formula (f), examples of lower alkylene groups which may optionally have phenyl group or lower alkylthio group and which is represented by B are $C_1$–$C_6$ straight- or branchedchain alkylene groups which may optionally have phenyl group or $C_1$–$C_6$ straight- or branched-chain alkylthio group, such as methylene, methylmethylene, ethylmethylene, isopropylmethylene, isobutylmethylene, tertbutylmethylene, ethylene, trimethylene, tetramethylene, 2-methyltrimethylene, pentamethylene, hexamethylene, phenylmethylene, benzylmethylene, 5-phenylpentylmethylene, 3-phenylhexamethylene, methylthiomethylene, 2-methylthioethylmethylene, hexylthiomethylene, isopropylthiomethylene, 3-tert-butylthiohexamethylene, etc. Examples of lower alkyl groups represented by $R^{10}$ and $R^{11}$ are straight- or branched-chain alkyl groups having 1 to 6 carbon atoms, such as methyl, ethyl, propyl, isopropyl, butyl, tert-butyl, pentyl, hexyl and the like.

The salts of 2'-deoxy-5-fluorouridine derivatives according to the invention include, for example, acid addition salts with an acid capable of forming a salt with an amino group of amino acid, salts with a base capable of forming a salt with a carboxyl group of acidic amino acid, and the like. Examples of useful acids capable of forming the salts are inorganic acids such as hydrogen chloride, hydrogen bromide, phosphoric acid, nitric acid, sulfuric acid, sulfurous acid and the like; and organic acides such as p-toluenesulfonic acid, methanesulfonic acid, tartaric acid, phthalic acid, furmaric acid, citric acid, maleic acid, malonic acid, lactic acid, succinic acid, ascorbic acid, linolenic acid, oleic acid, nicotinic acid, picrylsulfonic acid and the like. Examples of useful bases capable of forming the salts are sodium hydroxide, potassium hydroxide, sodium carbonate, etc.

The compounds of the invention represented by the formula (I) can be prepared by processes as shown below in Reaction schemes-1 and -2.

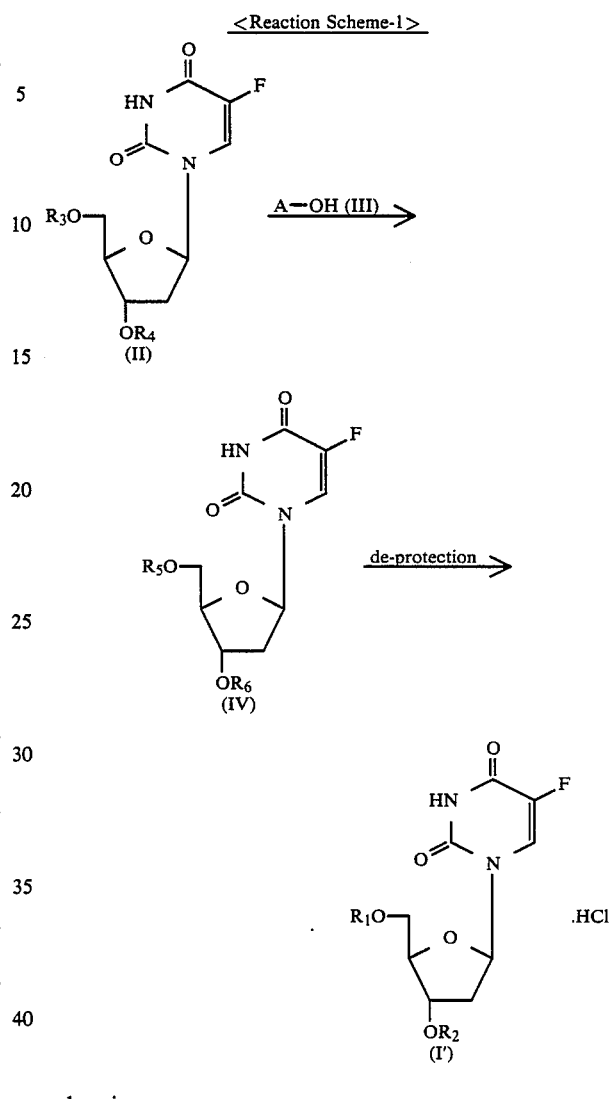

wherein:

$R_1$ and $R_2$ are as defined above, one of $R_3$ and $R_4$ is a hydrogen atom and the other is a benzyl group which may optionally have substituent selected from the group consisting of $C_1$–$C_6$ alkyl group, $C_1$–$C_6$ alkoxy group, $C_1$–$C_3$ halogenated alkyl group, halogen atom, hydroxyl group and nitro group on the phenyl ring, one of $R_5$ and $R_6$ is an amino acid residue having a protective group at the N-position and the other is an benzyl group which may optionally have substituent selected from the group consisting of $C_1$–$C_6$ alkyl group, $C_1$–$C_6$ alkoxy group, $C_1$–$C_3$ halogenated alkyl group, halogen atom, hydroxyl group and nitro group on the phenyl ring, and A is an amino acid residue having a protective group at the N-position.

The compound (IV) can be prepared by subjecting the compound (II) and the amino acid (III) to ester condensation. The amino acid can be used as it is or in the form of a reactive derivative such as a halide, acid anhydride or the like. Examples of the N-position protective group of the amino acid include those which are generally used in the art, for example, t-butoxycarbonyl (Boc), trichloroethoxycarbonyl, benzyloxycarbonyl, benzyloxycarbonyl groups which have 1 to 3 substituents such as methoxy, methyl, nitro and the like. The ester condensation of the compound (II) and the compound (III) is conducted usually in an anhydrous solvent in the presence of a basic compound and a condensation agent. Examples of useful solvents are aromatic hydrocarbons such as benzene, toluene, xylene and the like, halogenated hydrocarbons such as dichloromethane, chloroform, dichloroethane and the like, ethers such as ethyl ether, dioxane, tetrahydrofuran and the like, pyridine, nitromethane, dimethylformamide, etc. Examples of useful basic compounds are trialkylamine, pyridine, dialkylaminopyridine, picoline, lutidine and like tertiary amines, sodium carbonate, barium carbonate and like metal carbonates, etc., among which dialkylaminopyridine, in particular, di($C_1$–$C_3$ alkyl)aminopyridine such as dimethylaminopyridine, diethylaminopyridine or the like is most preferred. Examples of useful condensation agents are p-toluenesulfonyl chloride, 2,4,6-triisopropylbenzenesulfonyl chloride (TPS chloride) and like arylsulfonyl chlorides, alkylsulfonyl chloride (particularly $C_1$–$C_3$ alkylsulfonyl chloride such as methanesulfonyl chloride, ethanesulfonyl chloride or the like), N,N-dicyclohexylcarbodiimide (DCC), thionyl chloride, phosphorus oxychloride, etc. among which DCC and TPS chloride are preferably used. The amount of the compound (III) used is about 1 to about 1.5 moles per mole of the compound (II). The basic compound and the condensation agent are used both in an amount of about 1 to about 5 moles per mole of the compound (II). The reaction is carried out at a temperature of usually about −50° C. to room temperature.

The compound (IV) thus obtained is subjected to a reaction for removing the protective group, if so desired. This reaction is performed by conventional methods. For example, the reaction is effected using a 0.5–5N hydrochloric acid solution in the presence of a solvent. This reaction removes the group protecting the amino acid residue, producing a hydrochloride (I') of the compound (I). Useful solvents include methylene chloride, chloroform, tetrahydrofuran, dioxane and the like.

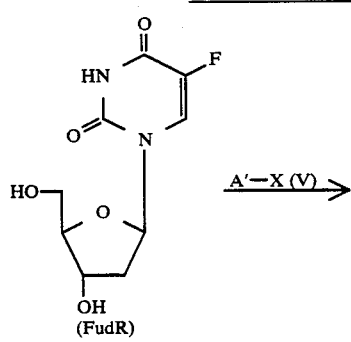

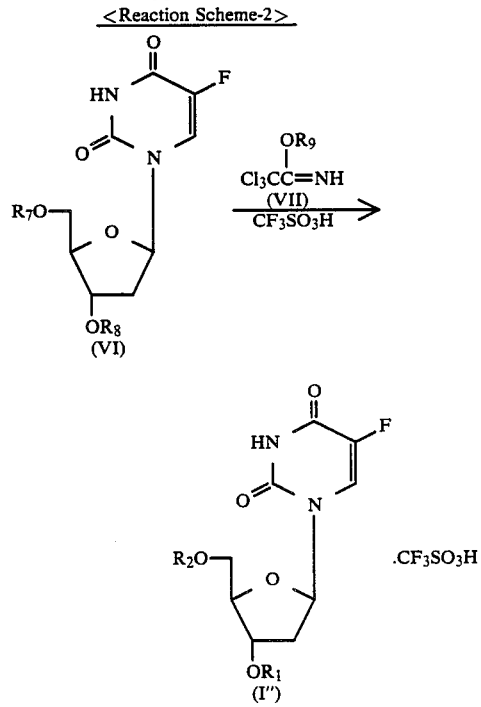

wherein:
$R_1$ and $R_2$ are as defined above, A' is an amino acid residue having a protective group at the N-position, X is a halogen atom, one of $R_7$ and $R_8$ is a hydrogen atom and the other is an amino acid residue having a protective group at the N-position, and $R_9$ is a benzyl group which may optionally have substituent selected from the group consisting of $C_1$–$C_6$ alkyl group, $C_1$–$C_6$ alkoxy group, $C_1$–$C_3$ halogenated alkyl group, halogen atom, hydroxyl group and nitro group on the phenyl ring.

The compound (VI) can be prepared by reacting FudR with the amino acid halide (V) in a solvent in the presence of a basic compound The compound (VI) is reacted with the substituted or unsubstituted benzylimidate (VII) in the presence of a trifluoromethanesulfonic acid, whereby the group protecting the amino acid residue is removed, giving the compound (I") in the form of a salt of trifluoromethanesulfonic acid.

Exemplary of the halogen atom represented by X in the formula (V) are chlorine and bromine.

Useful solvents and useful basic compounds include the examples mentioned above in the description of Reaction Scheme-1. About 1 to about 1.5 moles of the amino acid halide and about 0.1 to about 0.5 mole of the basic compound are used each per mole of FudR. The reaction is conducted at a temperature of about −50° C. to room temperature and is completed in about 2 to about 12 hours.

The reaction between the compound (VI) and the substituted or unsubstituted benzylimidate (VII) employs about 1 to about 5 moles of the compound (VII) and about 0.01 to about 0.5 mole of trifluoromethanesulfonic acid each per mole of the compound (VI). The solvents as exemplified above for the foregoing reaction can be used in this reaction. The reaction temperature is in the range of room temperature to approximately the boiling point of the solvent. The reaction time is about 2 to about 12 hours.

The hydrochloride of the compound of the invention and the trifluoromethanesulfonic acid salt thereof prepared in the processes in Reaction Schemes-1 and -2 can be converted into other desired salts by conventional salt exchange reactions heretofore commonly effected in the art. For example, the compound obtained in Reaction Scheme-1 or -2 is dissolved in an aqueous solution of sodium hydroxide, potassium hydroxide, sodium carbonate, sodium hydrogencarbonate or like base to neutralize the acid addition salt, and thereafter a desired acid component is added to produce the desired acid addition salt, followed by lyophilization.

The compounds of the invention prepared by the processes described above can be isolated by conventional separation methods such as column chromatography and can be purified by conventional purification methods such as recrystallization.

For use as a pharmaceutical composition, the derivative of the invention is combined with a pharmacologically acceptable suitable carrier and the mixture is made into a suitable preparation form according to a specific route of administration. Useful carriers include those already known in the art, for example, excipients, binders, lubricants, coloring agents, disintegrating agents, etc. Typical preparation forms of the pharmaceutical composition are, for example, tablets, capsules, granules, powders, liquids, injections for intravenous or like parenteral administration, suppository forms for introduction into rectum, etc.

The amount of the compound of the invention to be contained as effective component in a dosage unit of the pharmaceutical composition can be suitably determined according to the preparation form and does not widely vary from the amount in conventional pharmaceutical preparations. Usually a preferred amount of effective component is about 25 to about 500 mg per dosage unit. The compounds of the invention can be formulated into a suitable preparation form by conventional methods.

The dosage of the pharmaceutical composition thus obtained varies with the severity of symptoms, weight, age and other factors. The daily dosage is usually about 50 to 2000 mg calculated as the effective component. The pharmaceutical composition can be administered daily in a single dose or in 2 to 4 divided doses.

EXAMPLES

Given below are Examples and Preparation Examples, illustrative of the invention, and pharmacological test results to clarify the invention.

In connection with the NMR data in the examples, the numerals used as a superscript at the right of the symbol "H" or as a subscript at the right of the symbol "C" or "N" are used to refer to the position in the compound. Thus the term "$H^6$" or "$C_6$-H", for example, refers to the hydrogen bonded to the carbon atom at the 6-position. Similarly the term "$H^{3'}$, $H^{4'}$, $H^{5'}$ or "$C_{3',4',5'}$-H", for example, denotes the hydrogens bonded to the carbon atoms at the 3'-, 4'- and 5'-positions.

EXAMPLE 1

A 2.44 g quantity of $O^{3'}$-trityl-2'-deoxy-5-fluorouridine was dissolved in 15 ml of tetrahydrofuran (THF). Sodium hydride (0.5 g) was added and the mixture was stirred at 60° C. for 30 minutes A 0.63 g quantity of benzyl chloride and 0.375 g of sodium iodide were added and the mixture was reacted at 60° C. for 6 hours. The reaction mixture was neutralized with a 1N-HCl aqueous solution and concentrated. To the residue was added 20 ml of a 0.5 N-HCl solution in methanol and the mixture was stirred at room temperature overnight. The reaction mixture was neutralized with a saturated NaHCO₃ aqueous solution and concentrated. To the residue was added 20 ml of chloroform and the precipitate was collected by filtration. The precipitate was dissolved in ethyl acetate and the solution was washed with water, dried over Glauber's salt and concentrated, giving $O^{5'}$-benzyl-2'-deoxy-5-fluorouridine. The compound thus obtained was suspended in 15 ml of methylene chloride To the suspension were added 0.84 g of Boc-glycine, 1.24 g of DCC and 0.05 g of dimethylaminopyridine. The mixture was stirred at room temperature overnight. The reaction mixture was filtered and the filtrate was concentrated The residue was mixed with 5 ml of a 4N-HCl solution in dioxane, the mixture was stirred for 30 minutes and 20 ml of diethyl ether was added. The precipitated crystals were collected by filtration and purified with methanolethyl ether, giving 1.28 g of compound 1 shown below in Table 1.

EXAMPLE 2

The same procedure as in Example 1 was repeated with the exception of using the starting materials required for preparation of the desired compound. The procedure was repeated to produce compounds 2 to 11 and 28 to 30 shown below in Table 1.

EXAMPLE 3

A 2.44 g quantity of $O^{5'}$-trityl-2'-deoxy-5-fluorouridine was dissolved in 15 ml of THF. To the solution were added 0.5 g of powder of sodium hydroxide and 0.225 g of powder of Molecular Sieves 3A (trademark, product of Linde Co., U.S.A.). The mixture was refluxed with heating for 2 hours, followed by addition of 0.845 g of p-chlorobenzyl chloride and 0.15 g of sodium iodide The mixture was refluxed with heating for 2 hours and left to stand for cooling. The reaction mixture was filtered and the filtrate was neutralized with 15 ml of a saturated aqueous solution of ammonium chloride and washed with a saturated aqueous solution of sodium chloride. The organic layer was dried over Glauber's salt and concentrated. To the residue was added 20 ml of a 0.5N-HCl solution in methanol and the mixture was stirred overnight. The mixture was neutralized with a saturated NaHC03 aqueous solution and concentrated. THF (20 ml) was added to the residue and the mixture was washed with a saturated NaCl aqueous solution, dried over Glauber's salt and concentrated. The concentrate was recrystallized from ethanol, giving 1.32 g of $O^{3'}$-p-chlorobenzyl-2'-deoxy-5fluorouridine. In 12 ml of THF were dissolved 1.07 g of DCC and 0.73 g of Boc-glycine. To the solution were added 1.32 g of $O^{3'}$-chlorobenzyl-2'-deoxy-5-fluorouridine and 0.05 g of dimethylaminopyridine. The mixture was stirred at room temperature for 5 hours and filtered. The filtrate was concentrated and 5 ml of a 4N-HCl solution in dioxane was added to the residue. The mixture was stirred for 30 minutes after which 20 ml of diethyl ether was added. The precipitated crystals were filtered off and recrystallized from ethanol-isopropyl alcohol, giving 0.83 g of compound 12 shown below in Table 1.

EXAMPLE 4

The same procedure as in Example 3 was repeated, with the exception of using the starting compounds required for preparation of the desired compound, producing each of compounds 13 to 22 shown below in Table 1.

EXAMPLE 5

A 0.10 g quantity of O$^{3'}$-p-chlorobenzyl-O$^{5'}$-alanyl-2'-deoxy-5-fluorouridient.hydrochloride was dissolved in 4 ml of a 1:1 mixture of water and chloroform. To the solution was added 0.018 of NaHCO$_3$ with stirring. The mixture was stirred for 10 minutes, and the chloroform layer was separated. A solution of 0.10 g of 4-toluenesulfonic acid in 2 ml of methanol was added dropwise and a white sediment was filtered off and recrystallized from methanol-ethyl ether, giving 0.105 g of compound 23 shown below in Table 1.

EXAMPLE 6

The same procedure as in Example 5 was repeated, with the exception of using the starting compounds required for preparation of the desired compound, producing each of compounds 24 to 27 shown below in Table 1.

EXAMPLE 7

A 2.44 g quantity of 2'-deoxy-5-fluorouridine was dissolved in 25 ml of pyridine. Boc-glycyl chloride (0.97 g) was added and the mixture was reacted with ice-cooling for 3 hours. Thereafter the solvent was distilled off, water was added to the residue, the mixture was extracted with methylene chloride and the extract was dried over Glauber's salt and concentrated. The residue was dissolved in 25 ml of methylene chloride. To the solution were added 2.14 g of p-chlorobenzyl imidate and 0.75 g of trifluoromethanesulfonic acid. The mixture was reacted at room temperature for 3 hours and the solvent was distilled off. To the residue was added a saturated NaHCO$_3$ aqueous solution to render the solution alkaline. The solution was extracted with ethyl ether and the extract was dried over Glauber's salt. Hydrogen chloride was added, the precipitated crystals were filtered off and the filtrate was recrystallized from methanol-ethyl ether, giving 0.75 g of compound 12 shown below in Table 1.

Given below in Table 1 are the chemical structure and physico-chemical constants of compounds 1 to 30 prepared in Examples, 1 to 7.

TABLE 1

Compound 1
Structure:

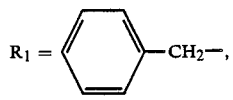

$R_2$=NH$_2$CH$_2$CO—
  Form (salt): Hydrochloride
  Crystal form: Amorphous
  Yield: 57.5%
  $^1$H-NMR TMS internal standard
  δ(DMSO-d$_6$)
  11.7–12.0 (b, 1 H, NH), 7.96 (d, 1 H, J=7 Hz, H$^6$), 7.34 (s, 5 H, aromatic), 6.14 (t, 1 H, J=7 Hz, H$^{1'}$), 4.54 (s, 2 H,

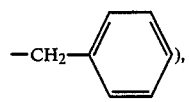

3.80–4.30 (m, 1H, H$^{4'}$), 3.85 (s, 2 H, NH$_2$CH$_2$CO$_2$—), 3.50–3.80 (m, 2 H, H$^{5'}$), 2.0–2.2 (m, 2H, H$^{2'}$).

Compound 2
Structure:

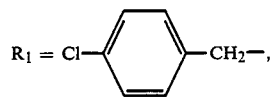

$R_2$=NH$_2$CH$_2$CO—
  Form (salt): Hydrochloride
  Yield: 63%
  $^1$H-NMR TMS internal standard
  δ(DMSO-d$_6$)
  11.6–12.0 (b, 1H, NH), 7.96 (d, 1H, H$^6$), 7.35 (s, 4H, aromatic), 6.20 (t, 1H, J=7 Hz, H$^{1'}$), 4.50 (s, 2 H,

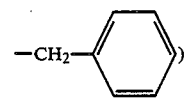

3.90–4.50 (m, 1H, H$^{4'}$), 3.50–3.90 (m, 2H, H$^{5'}$), 3.84 (s, 2H, NH$_2$CH$_2$CO$_2$—), 2.1–2.4 (m, 2H, H$^{2'}$).

Compound 3
Structure: $R_1$=NH$_2$CH$_2$CO—,

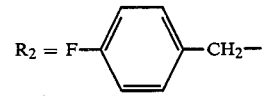

Form (salt): Hydrochloride
Yield: 71%
$^1$H-NMR TMS internal standard
δ(DMSO-d$_6$)
11.7–12.0 (b, 1H, NH), 7.95 (d, 1H, H$^6$), 7.0–7.6 (m, 4H, aromatic), 6.13 (t, 1 H, J=7 Hz, H$^{1'}$), 4.52 (s, 2H,

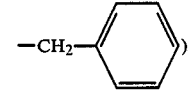

3.9–4.4 (m, 4H, H$^{3'}$, H$^{4'}$, H$^{5'}$), 3.85 (s, 2H, NH$_2$CH$_2$CO$_2$—), 3.64 (b, 2H, H$_2$O), 2.1–2.3 (m, 2 H, H$^{2'}$).

Compound 4
Structure: $R_1$=NH$_2$CH$_2$CO—,

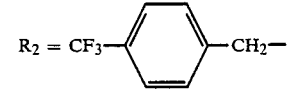

Form (salt): Hydrochloride
Yield: 62%
$^1$H-NMR TMS internal standard

δ(DMSO-d₆)

11.8–12.0 (b, 1H, NH), 7.98 (d, 1H, H⁶), 7.4–7.8 (m, 4H, aromatic), 6.14 (t, 1H, J=7 Hz, H¹'), 4.65 (s, 2H,

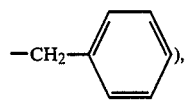

3.9–4.3 (m, 4H, H³', H⁴', H⁵'), 3.85 (s, 2H, NH₂CH₂CO₂—), 3.37 (b, 2H, H₂O), 2.0–2.5 (m, 2H, H²').

Compound 5
  Structure: R₁=NH₂CH₂CO—,

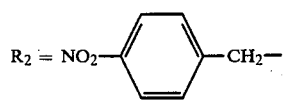

Form (salt): Hydrochloride
Yield: 52%
¹H-NMR TMS internal standard
δ(DMSO-d₆)

11.7–11.9 (b, 1H, NH), 7.95 (d, 1H, H⁶), 8.15 (d, J=9 Hz, aromatic), 7.62 (d, J=9 Hz, aromatic), 6.14 (t, 1H, J=7 Hz, H¹'), 4.70 (s, 2H,

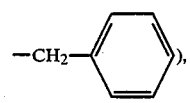

3.90–4.30 (m, 4H, H³', H⁴', H⁵'), 3.85 (s, 2H, NH₂CH₂CO₂—), 3.64 (b 2H₂O), 2.1–2.4 (m, 2H, H²').

Compound 6
  Structure: R₁=NH₂CH₂CO—,

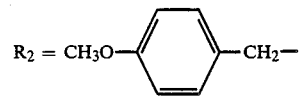

Form (salt): Hydrochloride
Yield: 72%
¹H-NMR TMS internal standard
δ(DMSO-d₆)

11.7–11.9 (b, 1H, NH), 8.01 (d, 1H, J=7 Hz, H⁶), 7.27 (2H, d, J=9 Hz, aromatic), 6.94 (2H, d, J=9 Hz, aromatic), 6.11 (t, 1H, J=7 Hz, H¹'), 4.45 (s, 2H,

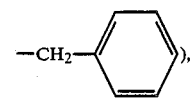

3.90–4.20 (m, 4H, H³', H⁴', H⁵'), 3.85 (s, 2H, NH₂CH₂CO₂13 ), 3.60 (b, 2H, H₂O), 2.10–2.40 (m, 2H, H²').

Compound 7
  Structure: R₁=NH₂CH₂CO—,

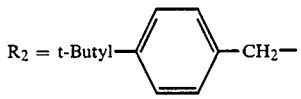

Form (salt): Hydrochloride
Yield: 65%
¹H-NMR TMS internal standard δ(DMSO-d₆)

11.8–12.0 (b, 1H, NH), 7.98 (d, 1H, J=7 Hz, H⁶), 7.20–7.60 (m, aromatic), 6.11 (t, 1H, J=7 Hz, H¹'), 4.49 (s, 2H,

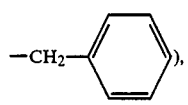

3.90–4.20 (m, 4H, H³', Hᵇ ⁴', H⁵'), 3.85 (s, 2H, NH₂CH₂CO—), 3.34 (b, 2H, H₂O), 2.00–2.40 (m, 2H, H²').

Compound 8
  Structure: R₁=NH₂CH₂CO—,

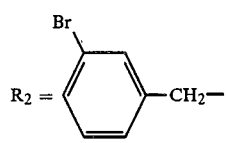

Form (salt): Hydrochloride
Yield: 78%
¹H-NMR TMS internal standard
δ(DMSO-d₆)

11.7–12.0 (b, 1H, NH), 7.99 (d, 1H, J=7 Hz, H⁶), 7.20–7.60 (m, 4H, aromatic), 6.13 (t,, 1H, J=7 Hz, H¹'), 4.54 (s, 2H,

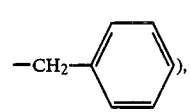

3.90–4.20 (m, 4H, H³', H⁴', H⁵'), 3.85 (s, 2H, NH₂CH₂CO₂—), 3.36 (b, 2H, H₂O), 2.0–2.40 (m, 2H, H²').

Compound 9
  Structure: R₁=NH₂CH₂CH₂CO—,

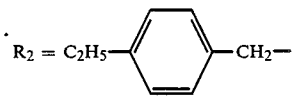

Form (salt): Hydrochloride
Yield: 63%
¹H-NMR TMS internal standard
δ(DMSO-d₆)

11.7–11.90 (b, 1H, NH), 8.10 (d, 1H, J=7 Hz, H⁶), 7.23 (s, 4H, aromatic), 6.12 (t, 1H, J=7 Hz, H¹'), 4.49 (s, 2H,

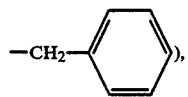), 3.90–4.20 (b, 4H, H$^{3'}$, H$^{4'}$, H$^{5'}$), 3.40 (b, 2H, H$_2$O), 2.97 (t, J=8 Hz, NH$_2$C$\underline{H_2}$CH$_2$CO$_2$—), 2.67 (t, J=8 Hz, NH$_2$CH$_2$C$\underline{H_2}$CO$_2$—), 2.66 (q, J=8 Hz,

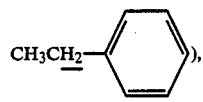), 2.12–2.40 (m, 2H, H$^{2'}$, 1.17 (t, J=8 Hz,

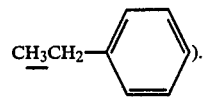).

Compound 10

Structure: R$_1$ = (CH$_3$)$_2$CHCHCO— (d compound),
$\overset{|}{\text{NH}_2}$

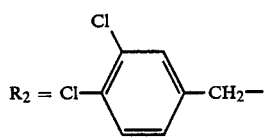

Form (salt): Hydrochloride
Yield: 79%
$^1$H-NMR TMS internal standard
δ(DMSO-d$_6$)
11.8–11.90 (b, 1H, NH), 7.98 (d, 1H, J=7 Hz, H$^6$), 7.20–7.60 (m, 3 H, aromatic), 6.13 (t, 1H, J=7 Hz, H$^{1'}$), 4.55 (s, 2H,

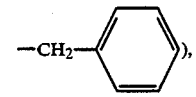), 4.00–4.40 (b, 4H, H$^{3'}$, H$^{4'}$, H$^{5'}$), 3.35 (b, 2H, H$_2$O), 2.10–2.50 (m, 2H, H$^{2'}$), 1.50–1.9 (m, 1H, (CH$_3$)$_2$C$\underline{H}$C(NH$_2$)HCO$_2$—), 0.7–1.2 (m, 6H, (C$\underline{H_3}$)$_2$CHC(NH$_2$)HCO$_2$—).
Compound 11
Structure: R$_1$=NH$_2$(CH$_2$)$_5$CO—,

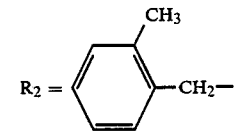

Form (salt): Hydrochloride
Yield: 76%
$^1$H-NMR TMS internal standard
δ(DMSO-d$_6$)
11.7–11.9 (b, 1H, NH), 8.00 (d, 1H, J=7 Hz, H$^6$), 7.1–7.2 (m, 4H, aromatic), 6.12 (t, 1H, J=7 Hz, H$^{1'}$), 4.52 (s, 2H,

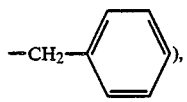), 4.0–4.4 (b, 4 H, H$^{3'}$, H$^{4'}$, H$^{5'}$), 3.34 (b, 2H, H$_2$O), 3.0 (t, J=8 Hz, NH$_2$(CH$_2$)$_4$C$\underline{H_2}$CO$_2$—), 2.10–2.50 (m, 2H, H$^{2'}$), 1.0–2.5 (m, 8H, N$\overline{\text{H}_2(\text{C}\underline{H_2})_4}$CH$_2$CO$_2$—), 2.29 (s, 3H,

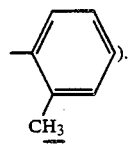).

Compound 12
Structure: R$_1$=NH$_2$CH$_2$CO—,

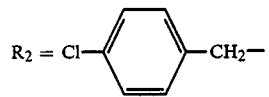

Form (salt): Hydrochloride
Crystal form: Amorphous
Yield: 72%
$^1$H-NMR TMS internal standard
δ(DMSO-d$_6$)
11.7–11.9 (b, 1H, NH), 8.02 (d, 1H, J=7 Hz, H$^6$), 7.40 (s, 4H, aromatic), 6.13 (t, 1H, J=7 Hz, H$^{1'}$), 4.55 (s, 2H,

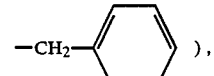), 4.04–4.4 (b, 4H, H$^{3'}$, H$^{4'}$, H$^{5'}$), 3.84 (s, 2H, NH$_2$C$\underline{H_2}$CO$_2$—), 3.34 (bs, 2H, H$_2$O), 2.10–2.50 (m, 2H, H$^{2'}$).
Compound 13

Structure: R$_1$ = CH$_3$CHCO—,
$\overset{|}{\text{NH}_2}$

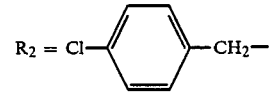

Form (salt): Hydrochloride
Yield: 78%
$^1$H-NMR TMS internal standard
δ(DMSO-d$_6$)
11.8–12.0 (b, 1H, NH), 8.00 (d, 1H, J=7 Hz, H$^6$), 7.40 (s, 4H, aromatic), 6.12 (t, 1H, J=7 Hz, H$^{1'}$), 4.55 (s, 2H,

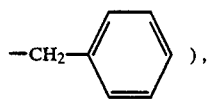), 3.90–4.4 (b, 4H, H$^{3'}$, H$^{4'}$, H$^{5'}$), 4.00 (m, 1H, CH$_3$C(NH$_2$)$\underline{H}$CO$_2$—), 3.35 (bs, 2H, H$_2$O), 2.10–2.50 (m, 2H, H$^{2'}$), 1.4$\overline{3}$ (d, 3H, J=8 Hz, C$\underline{H}_3$C(NH$_2$)HCO$_2$—).
Compound 14

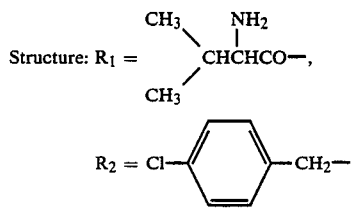

Form (salt): Hydrochloride
Yield: 82%
$^1$H-NMR TMS internal standard
δ(DMSO-d$_6$)
11.0–11.5 (b, 1H, NH), 7.95 (d, 1H, J=7 Hz, H$^6$), 7.35 (s, 4H, aromatic), 6.10 (t, 1H, J=7 Hz, H$^{1'}$), 4.50 (s, 2H,

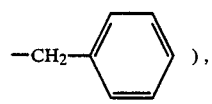), 4.00–4.40 (b, 4H, H$^{3'}$, H$^{4'}$, H$^{5'}$), 3.80 (d, 1H, (CH$_3$)$_2$CHC((NH$_2$)$\underline{H}$CO$_2$—, 3.30 (bs, 2H, H$_2$O), 2.10–2.50 (m, 2H, H$^{2'}$), 1.50–1.90 (b, 1H, (CH$_3$)$_2$C$\underline{H}$C(NH$_2$)HCO$_2$—), 0.70–1.10 (m, 6H, (C$\underline{H_3}$)$_2$$\overline{C}$HC(NH$_2$)NCO$_2$—).
Compound 15

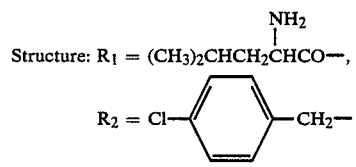

Form (salt): Hydrochloride
Yield: 77%
$^1$H-NMR TMS internal standard
δ(DMSO-d$_6$)
11.50–11.90 (b, 1H, NH), 7.96 (d, 1H, J=7 Hz, H$^6$), 7.40 (s, 4H, aromatic), 6.15 (t, 1H, J=7 Hz, H$^{1'}$), 4.53 (s, 2H,

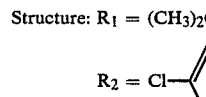), 3.60–4.20 (m, 4H, H$^{3'}$, H$^{4'}$, H$^{5'}$), 3.25 (t, 1H, J=11 Hz, (CH$_3$)$_2$CHCH$_2$C(NH$_2$$\underline{H}$CO$_2$—), 2.12–2.50 (m, 2H, H$^{2'}$), 1.20–1.90 (m, 3H, (CH$_3$)$_2$C$\underline{H}$C$\underline{H_2}$C(NH$_2$)HCO$_2$—), 1.00 (s, 3H,

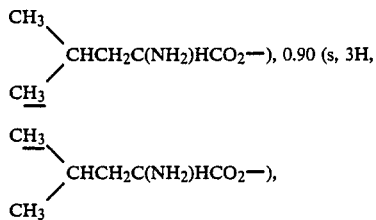

CHCH$_2$C(NH$_2$)HCO$_2$—), 0.90 (s, 3H,

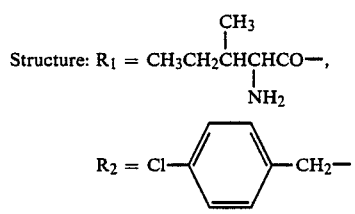

Compound 16

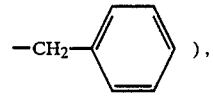

Form (salt): Hydrochloride
Yield: 81%
$^1$H-NMR TMS internal standard
δ(DMSO-d$_6$)
11.50–12.00 (b, 1H, NH), 8.00 (d, 1H, J=7 Hz, H$^6$), 7.40 (s, 4H, aromatic), 6.15 (t, 1H, J=7 Hz, H$^{1'}$), 4.60 (s, 2H,

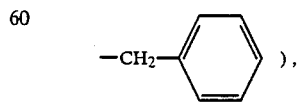), 4.01–4.42 (m, 4H, H$^{3'}$(m, 4H, H$^{3'}$, H$^{4'}$, H$^{5'}$), 3.85 (d, 1H, J=6 Hz, CH$_3$CH$_2$C(CH$_3$)HC(NH$_2$)$\underline{H}$CO$_2$—), 3.20–3.40 (m, 2H, H$_2$O), 2.20–2.40 (b, $\overline{2}$H, H$^{2'}$), 1.80–2.40 (b, 1H, CH$_3$CH$_2$C(CH$_3$)$\underline{H}$C(NH$_2$)HCO$_2$—), 0.70–1.80 (m, 8H, C$\underline{H_3}$C$\underline{H_2}$C(CH$_3$)$\overline{H}$C(NH$_2$)HCO$_2$—).
Compound 17

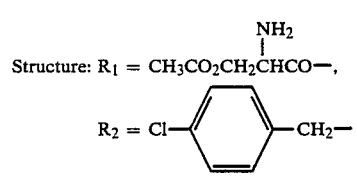

Form (salt): Hydrochloride
Yield: 75%
$^1$H-NMR TMS internal standard
δ(DMSO-d$_6$)
11.8–12.0 (b, 1H, NH), 8.22 (d, 1H, J=7 Hz, H$^6$), 7.41 (s, 4H, aromatic), 6.14 (t, 1H, J=7 Hz, H$^{1'}$), 4.61 (s, 2H,

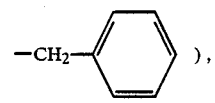), 4.00–4.40 (m, 4H, H$^{3'}$, H$^{4'}$, H$^{5'}$), 3.20–3.40 (m, 2H, H$_2$O), 2.10–2.50 (b, 2H, H$^{2'}$), 2.0 (s, 3H, CH$_3$CO$_2$CH$_2$C(NH$_2$)HCO$_2$—).
Compound 18

Structure: $R_1$ = $CH_3SCH_2CH_2CHCO-$, 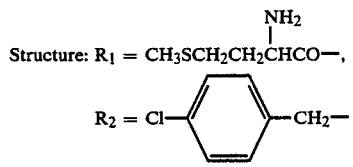

$R_2$ = 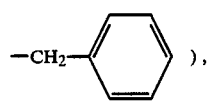

Form (salt): Hydrochloride
Yield: 74%
$^1$H-NMR TMS internal standard
$\delta(DMSO-d_6)$
11.80–12.00 (b, 1H, NH), 7.98 (d, 1H, J=7 Hz, $H^6$), 7.38 (s, 4H, aromatic), 6.10 (t, 1H, J=7 Hz, $H^{1'}$), 4.52 (s, 2H, $-CH_2-\phantom{x}$), 3.95–4.45 (b, 4H, $H^{3'}$, $H^{4'}$, $H^{5'}$), 3.15–3.45 (m, 2H, $H_2O$), 3.40 (t, 1H, $CH_3SCH_2CH_2C(NH_2)\underline{H}CO_2-$), 2.85–2.90 (m, 2H, $CH_3SCH_2\underline{CH_2}C(NH_2)HCO_2-$), 2.20–2.40 (b, 2H, $H^{2'}$), 2.20 (s, 3H, $C\underline{H_3}SCH_2CH_2C(NH_2)HCO_2-$), 1.50–1.60 (m, 2H, $CH_3S\underline{CH_2}CH_2C(NH_2)HCO_2-$).
Compound 19

Structure: $R_1$ = 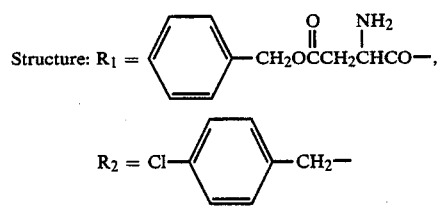

$R_2$ = Cl—⟨ ⟩—$CH_2$—

Form (salt): Hydrochloride
Yield: 73%
$^1$H-NMR TMS internal standard
$\delta(DMSO-d_6)$
11.8–12.0 (b, 1H, NH), 8.00 (d, 1H, J=7 Hz, $H^6$), 7.39 (s, 4H, aromatic), 7.35 (s, 4H, ⟨ ⟩—$CH_2OCOCH_2C(NH_2)HCO_2-$), 6.11 (t, 1H, J = 7 Hz, $H^{1'}$), 5.11 (s, 2H, ⟨ ⟩—$C\underline{H_2}OCOCH_2C(NH_2)HCO_2-$), 4.52 (s, 2H, $-CH_2-$⟨ ⟩), 3.95–4.40 (b, 4H, 3.95–4.40 (b, 4H, $H^{3'}$, $H^{4'}$, $H^{5'}$), 3.10 (bs, 2H, $H_2O$), 2.10–2.40 (b, 2H, $H^{2'}$).
Compound 20

Structure: $R_1$ = $NH_2(CH_2)_4CHCO-$, 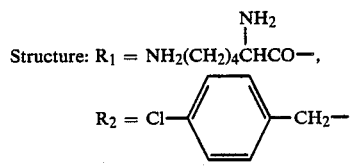

$R_2$ = Cl—⟨ ⟩—$CH_2$—

Form (salt): Hydrochloride

Yield: 26%
$^1$H-NMR TMS internal standard
$\delta(DMSO-d_6)$
11.45–11.90 (b, 1H, NH), 7.95 (d, 1H, J=7 Hz, $H^6$), 7.35 (s, 4H, aromatic), 6.13 (t, 1H, J=7 Hz, $H^{1'}$), 4.50 (s, 2H, $-CH_2-$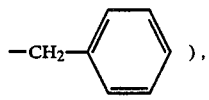), 3.95–4.45 (b, 4H, $H^{3'}$, $H^{4'}$, $H^{5'}$), 3.10–3.65 (b, 1H, $NH_2(CH_2)_4C(NH_2)\underline{H}CO_2-$), 3.20–3.40 (m, 2H, $H_2O$), 2.65–3.10 (b, 2H, $\overline{NH_2}CH_2(C\underline{H_2})_3C(NH_2)HCO_2-$), 2.10–2.50 (m, 2H, $H^{2'}$), 1.00–2.10 (b, 6H, $NH_2CH_2(C\underline{H_2})_3C(NH_2)HCO_2-$).
Compound 21

Structure: $R_1$ = 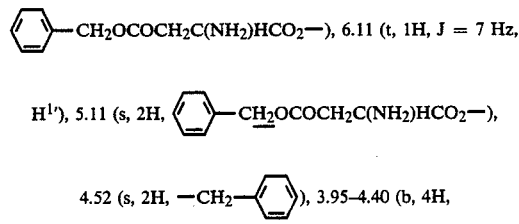

$R_2$ = Cl—⟨ ⟩—$CH_2$—

Form (salt): Hydrochloride
Yield: 79%
$^1$H-NMR TMS internal standard
$\delta(DMSO-d_6)$
11.90 (b, 1H, NH), 8.00 (d, 1H, J=8 Hz, $H^6$), 7.40 (s, 4H, aromatic), 7.23 (s, 5H, aromatic, ⟨ ⟩—$CH_2C(NH_2)HCO_2-$), 6.10 (t, 1H, J = 8 Hz, $H^{1'}$), 4.50 (s, 2H, $-CH_2-$⟨ ⟩), 4.00–4.40 (b, 5H, $H^{3'}$, $H^{4'}$, $H^{5'}$, ⟨ ⟩—$CH_2C(NH_2)\underline{H}CO_2-$), 3.20–3.50

(m, 2H, $H_2O$), 3.19 (s, 2H, ⟨ ⟩—$C\underline{H_2}C(NH_2)HCO_2-$), 2.00–2.15 (b, 2H, $H^{2'}$), 1.08 (t, 1H, J=8 Hz, diethyl ether (solvent)).
Compound 22

Structure: $R_1$ = 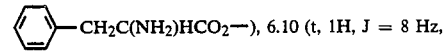

$R_2$ = Cl—⟨ ⟩—$CH_2$—

Form (salt): ½.tartrate
Yield: 80%
$^1$H-NMR TMS internal standard
$\delta(DMSO-d_6)$ 7.60 (s, 1H, 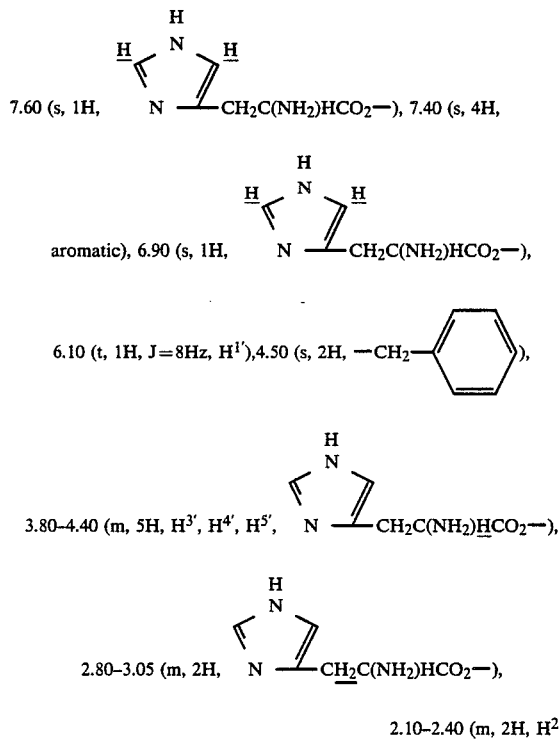—CH₂C(NH₂)HCO₂—), 7.40 (s, 4H, aromatic), 6.90 (s, 1H, —CH₂C(NH₂)HCO₂—), 6.10 (t, 1H, J=8Hz, H¹'), 4.50 (s, 2H, —CH₂—⌬), 3.80-4.40 (m, 5H, H³', H⁴', H⁵', —CH₂C(NH₂)<u>H</u>CO₂—), 2.80-3.05 (m, 2H, —C<u>H</u>₂C(NH₂)HCO₂—), 2.10-2.40 (m, 2H, H²').

Compound 23

Structure: R₁ = CH₃CHCO—,
              |
              NH₂

R₂ = Cl—⌬—CH₂—

Form (salt): CH₃—⌬—SO₃H salt

Crystal form: Amorphous
Yield: 82%
¹H-NMR TMS internal standard
δ(DMSo-d₆)
11.65-12.00 (b, 1H, NH), 7.95 (d, 1H, J=8 Hz, H⁶), 7.20, 7.38, 7.78 and 7.90 (s, 4H,

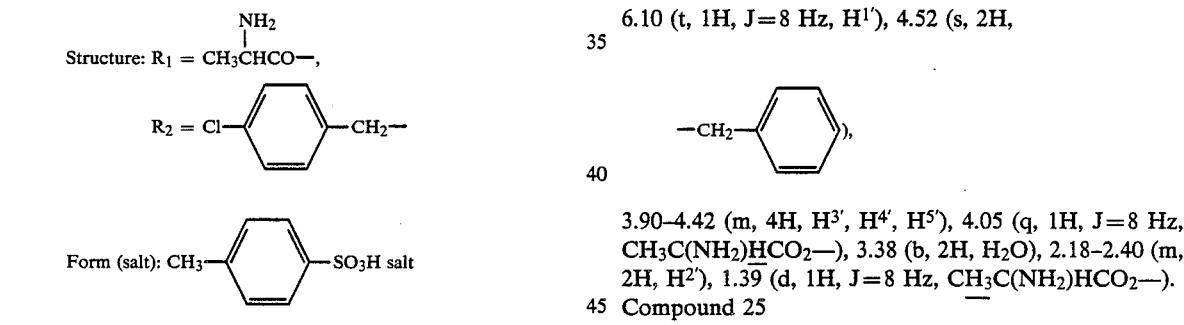

1H, J=8Hz, H¹'), 4.55 (s, 2H, —CH₂—⌬), 3.90-4.40 (m, 4H, H³', H⁴', H⁵'), 3.72, (m, 1H, CH₃C(NH₂)<u>H</u>CO₂—), 3.38 (s, 2H, H₂O), 2.20-2.40 (b, 2H, H²'), 2.23 (s, 3H,

CH₃—⌬—SO₃H), 1.40 (d, 3H, J=8 Hz, C<u>H</u>₃C(NH₂)HCO₂—).

Compound 24

Structure: R₁ = CH₃CHCO—,
              |
              NH₂

R₂ = Cl—⌬—CH₂—

Form (salt): ½·maleate
Yield: 38%
¹H-NMR TMS internal standard
δ(DMSO-d₆) 12.45 (s, 1H, C<u>H</u>COOH
‖
C<u>H</u>COOH), 7.95 (d, 1H, J=8 Hz, H⁶), 7.40 (s, 4H, aromatic), 6.30 (s, 1H, C<u>H</u>COOH
‖
C<u>H</u>COOH), 6.10 (t, 1H, J=8 Hz, H¹'), 4.52 (s, 2H,

—CH₂—⌬), 3.90-4.42 (m, 4H, H³', H⁴', H⁵'), 4.05 (q, 1H, J=8 Hz, CH₃C(NH₂)<u>H</u>CO₂—), 3.38 (b, 2H, H₂O), 2.18-2.40 (m, 2H, H²'), 1.39 (d, 1H, J=8 Hz, C<u>H</u>₃C(NH₂)HCO₂—).

Compound 25

Structure: R₁ = CH₃CHCO—,
              |
              NH₂

R₂ = Cl—⌬—CH₂—

Form (salt): ½·tartrate
Yield: 57%
¹H-NMR TMS internal standard
δ(DMSO-d₆)
11.80-12.00 (b, 1H, NH), 7.98 (d, 1H, J=8 Hz, H⁶), 7.39 (s, 4H, aromatic), 6.10 (t, 1H, J=8 Hz, H¹'), 4.50 (s, 2H, Hz, H¹'), 4.50 (s, 2H, —CH₂—⌬), 4.00-4.50

(m, 4H, H³', H⁴', H⁵'), 4.40 (s, 1H, HOC̲H
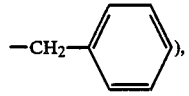
), 4.00 (m, 1H, CH₃C(NH₂)H̲CO₂—), 3.40 (b, 2H, H₂O), 2.20–2.40 (m, 2H, H²'), 1.40 (d, 3H, J=8 Hz, CH̲₃C(NH₂)HCO₂—).

Compound 26

Structure: R₁ = 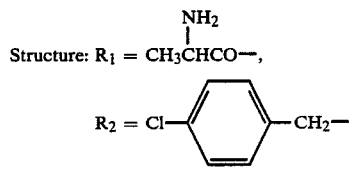,

R₂ = 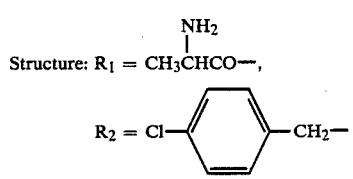

Form (salt): ½.citrate
Yield: 74%
¹H-NMR TMS internal standard
δ(DMSO-d₆)
11.70–12.10 (b, 1H, NH), 10.0–12.0 (b, 2H,
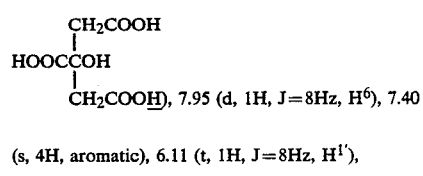
), 7.95 (d, 1H, J=8Hz, H⁶), 7.40 (s, 4H, aromatic), 6.11 (t, 1H, J=8Hz, H¹'), 4.51 (s, 2H, —CH₂—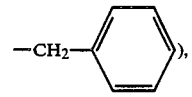), 4.00–4.50 (m, 4H, H³', H⁴', H⁵'), 4.05 (m, 1H, CH₃C(NH₂)H̲CO₂—), 3.35

(b, 2H, H₂O), 2.72 (s, 2H, 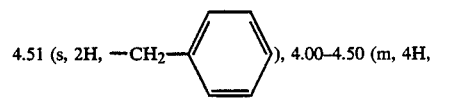), 2.20–2.39 (m, 2H, H²'), 1.39 (d, 3H, J=8 Hz, CH̲₃C(NH₂)HCO₂—).

Compound 27

Structure: R₁ = 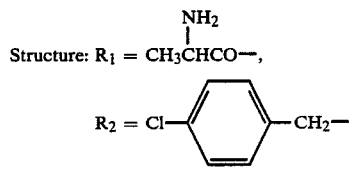,

R₂ = 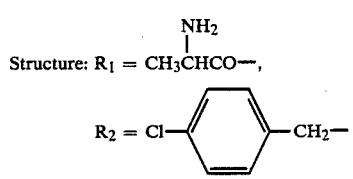

Form (salt): Phosphate
Yield: 40%
¹H-NMR TMS internal standard
δ(DMSO-d₆)
11.65–12.00 (b, 1H, NH), 7.90 (d, 1H, J=8 Hz, H⁶), 7.40 (s, 4H, aromatic), 6.05 (t, 1H, J=8 Hz, H¹'), 4.50 (s, 2H, —CH₂—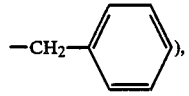), 4.00–4.50 (m, 4H, H³', H⁴', H⁵'), 4.00 (m, 1H, CH₃C(NH₂)H̲CO₂—), 3.35 (b, 2H, H₂O), 2.15–2.40 (m, 2H, H²'), 1.40 (d, 3H, J=8 Hz, CH̲₃C(NH₂)HCO₂—).

Compound 28

Structure: R₁ = NH₂CH₂CO—,

R₂ = Cl—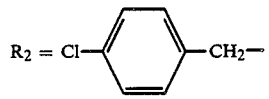—CH₂—

Form (salt):
Yield: 75%
¹H-NMR TMS internal standard
δ(DMSO-d₆)
11.80–12.00 (b, 1H, NH), 7.90 (d, 1H, J=8 Hz, H⁶), 7.40 (s, 4H, aromatic), 6.15 (t, 1H, J=8 Hz, H¹'), 4.54 (s, 2H, —CH₂—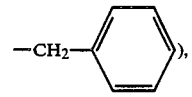), 4.00–4.50 (m, 4H, H³', H⁴', H⁵'), 4.06 (2H, s, NH₂C̲H₂CO₂—), 3.32 (b, 2H, H₂O), 2.10–2.50 (m, 2H, H²').

Compound 29

Structure: R₁ = 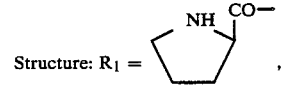,

R₂ = Cl—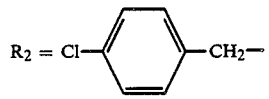—CH₂—

Form (salt): Hydrochloride
Yield: 63%
¹H-NMR TMS internal standard
δ(DMSO-d₆)
11.80–12.10 (b, 1H, NH), 8.03 (d, 1H, J=8 Hz, H⁶), 9.3–10.2 (b, 1H,

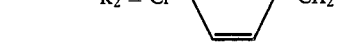), 7.41 (s, 4H, aromatic), 6.13 (t, 1H, J=8 Hz, H¹'), 4.56 (s, 2H,

—CH₂—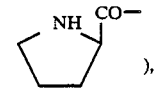), 4.00–4.50 (m, 4H, H³', H⁴', H⁵'), 3.22 (b, 2H, H₂O), 2.00–2.50 (m, 2H, H²').

Compound 30

Structure: $R_1 = NH_2CH_2CO-$,

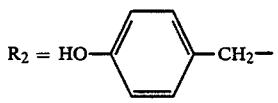

Form (salt): Hydrochloride
Yield: 53%
$^1$H-NMR TMS internal standard
δ(DMSO-d$_6$)
11.7–11.9 (b, 1H, NH), 9.37 - (bs,

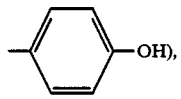

7.92 (d, 1H, J=8 Hz, H$^6$), 7.14 (d, J=8 Hz, 2H, aromatic), 6.70 (d, J=8 Hz, 2H, aromatic), 6.08 (t, 1H, J=8 Hz, H$^{1'}$), 4.52 (s, 2H,

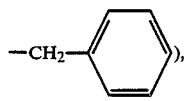

4.0–4.4 (m, 4H, H$^{3'}$, H$^{4'}$, H$^{5'}$), 3.82 (s, 2H, NH$_2$C$\underline{H_2}$CO$_2$—), 3.35 (bs, 2H, H$_2$O), 2.0–2.45 (m, 2H, H$^{2'}$).

EXAMPLE 8

(A) Preparation of 5'-O-[N-(t-butoxycarbonyl)-glycyl]-3'-O-(4-chlorobenzyl)-2'-deoxy-5-fluorouridine To a solution of 9.45 g of N-(t-butoxycarbonyl)-glycine in 60 ml of acetonitrile was added 6.13 g of dicyclohexylcarbodiimide with stirring under ice-cooling. After three hours, dicyclohexylurea produced was filtered off, and the filtrate was concentrated. The oily residue was dissolved in 15 ml of anhydrous pyridine, and to the solution was added 5.00 g of 3'-O-(4-chlorobenzyl)-2'-deoxy-5-fluorouridine. The mixture was left to stand for three hours at room temperature and for 30 minutes at a temperature of 40° C. To the mixture was added 5 ml of water at room temperature and the mixture was left to stand for 30 minutes and then concentrated. The residue was dissolved in 50 ml of ethyl acetate, and the solution was washed three times with saturated aqueous solution of sodium hydrogen carbonate and twice with saturated aqueous solution of sodium chloride. Further the solution was dried over anhydrous magnesium sulfate and concentrated. The residue was placed on silica gel column and eluted with 1% methanol-chloroform, giving 5.33 g (75%) of 5'-O-[N-(t-butoxycarbonyl)glycyl]-3'-O-(4-chlorobenzyl)-2'-deoxy-5-fluorouridine.

NMR (DMSO-d$_6$) δ: 11.85 (1H, bs, NH), 7.94 (1H, d, J=7Hz, C$_6$-H), 7.40 (4H, s, C$_6$H$_4$Cl), 7.20 (1H, t, J=6Hz, OCONH), 6.14 (1H, t, J=6 Hz, C$_{1'}$-H), 4.54 (2H, s, CH$_2$C$_6$H$_4$Cl), 4.30–4.16 (4H, m, C$_{3',4',5'}$-H), 3.74 (2H, d, J=6 Hz, CH$_2$CO), 2.38–2.32 (2H, m, C$_{2'}$-H), 1.37 (9H, s, CH$_3$×3)

(B) and (C)

Following the procedure as described above in (A) and using appropriate starting materials, the compounds shown in Table 2 were prepared. In Table 2, compounds are indicated with R$_2$ and R$_1$ groups in the formula (I). This is applied to the following tables. Also in Table 2 and subsequent tables, the term "Str" means structure.

TABLE 2

Example 8 (B)

Str:

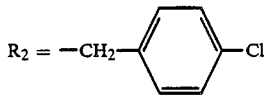

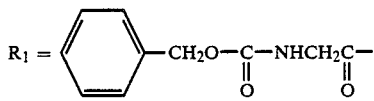

Yield: 43%
NMR (DMSO-d$_6$) δ:
11.85 (1H, s, NH)
7.93 (1H, d, J=7Hz, C$_6$—H)
7.69 (1H, t, J=6Hz, OCONH)
7.39 (4H, s, C$_6$H$_4$Cl)
7.33 (5H, s, C$_6$H$_5$)
6.13 (1H, t, J=6Hz, C$_{1'}$—H)
5.04 (2H, s, C$\underline{H_2}$C$_6$H$_5$)
4.53 (2H, s, C$\underline{H_2}$C$_6$H$_4$Cl)
4.30–4.14 (4H, m, C$_{3',4',5'}$—H)
3.83 (2H, d, J=6Hz, CH$_2$CO)
2.37–2.27 (2H, m, C$_{2'}$—H)

Example 8 (C)

Str:

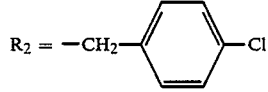

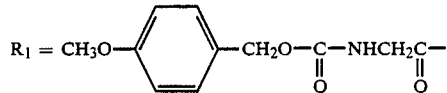

Yield: 73%
NMR (DMSO-d$_6$) δ:
11.86 (1H, bs, NH)
7.92 (1H, d, J=7Hz, C$_6$—H)
7.62 (1H, t, J=6Hz, OCONH)
7.40 (4H, s, C$_6$H$_4$Cl)
7.29 (2H, d, J=9Hz, C$_{3'5}$—H of the methoxybenzyl)
6.90 (2H, d, J=9Hz, C$_{2'6}$—H of the methoxybenzyl)
6.15 (1H, t, J=6Hz, C$_{1'}$—H)
4.97 (2H, s, CH$_2$C$_6$H$_4$OCH$_3$)
4.53 (2H, s, C$\underline{H_2}$C$_6$H$_4$Cl)
4.30–4.19 (4H, m, C$_{3',4',5'}$—H)
3.84 (2H, d, J=6Hz, CH$_2$CO)
3.74 (3H, s, OCH$_3$)
2.32-2.20 (2H, m, C$_{2'}$—H)

(D) Preparation of 5'-O-(N-benzyloxycarbonyl)glycyl-3'-O-(4-chlorobenzyl)-2'-deoxy-5-fluorouridine To a solution of 1.00 g of 3'-O-(4-chlorobenzyl)-2'-deoxy-5-fluorouridine in 20 ml of pyridine was added 1.23 g of N-benzyloxycarbonylglycine chloride, and the mixture was subjected to reaction at room temperature for two days.

The reaction mixture was concentrated under reduced pressure, and to the residue were placed 30 ml of ethyl acetate and 20 ml of water. The organic layer was separated from the solution and dried over anhydrous magnesium sulfate, and the solvent was distilled off. The resulting oily residue was placed on silica gel column and eluted with 1% methanol-chloroform for purification, giving 0.26 g (17%) of the desired 5'-O-(N-benzyloxycarbonyl)glycyl-3'-O-(4-chlorobenzyl)-2'-deoxy-5-fluorouridine.

The product thus obtained was identified to be the compound provided in Example 8 (B) by thin-layer chromatography (developing solvent; chloroform:methanol=39:2, detection; irradiation with UV rays).

(E) Preparation of 3'-0-(4-chlorobenzyl)-2'-deoxy-5-fluoro-5'-O-glycyluridine hydrochloride In 3 ml of 4N-HCl-dioxane was dissolved 0.88 g of 5'—O—[N-(t-butoxycarbonyl)glycyl]-3'-O-(4-chlorobenzyl)- 2'-deoxy-5-fluorouridine obtained in Example 8 (A), and the solution was left to stand for 30 minutes at room temperature. The solvent was distilled off and the residue was placed on silica gel column and eluted with 4-6% methanol-chloroform, giving 0.36 g (45%) of 3'-O-(4-chlorobenzyl)-2'-deoxy-5-fluoro-5'-O-glycyluridine hydrochloride.

Form: Hygroscopic powder
NMR (DMSO-$d_6$) δ:
11.83 (1H, bs, NH), 8.68 (3H, bs, $NH_2$, HCl), 8.04 (1H, d, J=7 Hz, $C_6$-H), 7.41 (4H, s, $C_6H_4Cl$), 6.15 (1H, t, J=6 Hz, $C_{1'}$-H), 4.56 (2H, s, $CH_2C_6H_4Cl$), 4.41-4.15 (4H, m, $C_{3',4',5'}$-H), 3.83 (2H, s, $\underline{CH_2}CO$), 2.44-1.99 (2H, m, $C_{2'}$-H)

Elemental analysis: for $C_{18}H_{19}ClFN_3O_6 \cdot HCl \cdot H_2O$
Calcd.: C, 44.83%; H, 4.60%; N, 8.71%, Found : C, 44.64%; H, 4.91%; N, 8.43%

EXAMPLES 9–17

Using appropriate starting materials, the procedure of Example 8 (A) and then the procedure of Example 8 (E) were followed, thereby giving the compounds shown below in Table 3. However, the contemplated compound in Example 12 was obtained by following the procedure of Example 8 (A).

TABLE 3

Example 9

Str: $R_2 = -CH_2-\langle C_6H_5 \rangle$ $R_1 = HCl \cdot NH_2CH_2\overset{O}{\underset{\|}{C}}-$ Yield: 27%
Form: Hygroscopic powder
NMR (DMSO-$d_6$) δ:
11.83(1H, bs, NH)
8.54(3H, bs, $NH_2$, HCl)
8.01(1H, d, J=7Hz, $C_6$-H)
7.35(5H, s, $C_6H_5$)
6.14(1H, t, J=6Hz, $C_{1'}$-H)
4.56(2H, s, $\underline{CH_2}C_6H_5$)
4.40-4.16(4H, m, $C_{3',4',5'}$-H)
3.82(2H, s, $\underline{CH_2}CO$)
2.42-2.29(2H, m, $C_{2'}$-H)

Example 10

Str: $R_2 = -CH_2-\langle C_6H_4 \rangle-OCH_3$ $R_1 = HCl \cdot NH_2CH_2\overset{O}{\underset{\|}{C}}-$ Yield: 28%
Form: Hygroscopic powder
NMR (DMSO-$d_6$) δ:
11.86(1H, bs, NH)
9.48(3H, bs, $NH_2$, HCl)

TABLE 3-continued 8.04(1H, d, J=7Hz, $C_6$-H)
7.29(2H, d, J=8Hz, $C_{3,5}$-H of the benzene ring)
6.94(2H, d, J=8Hz, $C_{2,6}$-H of the benzene ring)
6.13(1H, t, J=6Hz, $C_{1'}$-H)
4.48(2H, s, $\underline{CH_2}C_6H_4$-$OCH_3$)
4.39-4.18(4H, m, $C_{3',4',5'}$-H)
3.82(2H, s, $CH_2CO$)
2.37-2.28(2H, m, $C_{2'}$-H)

Example 11

Str: $R_2 = -CH_2-\langle C_6H_4 \rangle$-Br (ortho)

$R_1 = HCl \cdot NH_2CH_2\overset{O}{\underset{\|}{C}}-$

Yield: 88%
Form: Hygroscopic powder
NMR (DMSO-$d_6$) δ:
11.86(1H, bs, NH)
8.67(3H, bs, $NH_2$, HCl)
8.04(1H, d, J=7Hz, $C_6$-H)
7.68-7.25(4H, m, $C_6H_4Br$)
6.17(1H, t, J=6Hz, $C_{1'}$-H)
4.60(2H, s, $\underline{CH_2}C_6H_4Br$)
4.43-4.20(4H, m, $C_{3',4',5'}$-H)
3.83(2H, s, $CH_2CO$)
2.41-2.35(2H, m, $C_{2'}$-H)

Example 12

Str: $R_2 = -CH_2-\langle C_6H_4 \rangle-Cl$ $R_1 = -\overset{O}{\underset{\|}{C}}-CH_2CH_2-N\langle \text{piperidine} \rangle \cdot HCl$ Yield: 26%
Form: Hygroscopic powder
NMR (DMSO-$d_6$) δ:
11.83(1H, bs, NH)
10.82(1H, bs, HCl)
7.98(1H, d, J=7Hz, $C_6$-H)
7.41(4H, s, $C_6H_4Cl$)
6.23-6.06(1H, m, $C_{1'}$-H)
4.55(2H, s, $\underline{CH_2}C_6H_4Cl$)
4.33-4.16(4H, m, $C_{3',4',5'}$-H)
3.46-2.79(8H, m, $-CH_2CH_2-N\langle \text{piperidine} \rangle)$ 2.46-2.28(2H, m, $C_{2'}$-H)

1.87-1.40 (6H, m, $-N\langle \text{piperidine ring} \rangle)$

Example 13

TABLE 3-continued

Str: R₂ = —CH₂—C₆H₄—Cl (para)

R₁ = HCl.NH₂—CH—C(=O)—
       |
       CH(CH₃)₂  (L)

Yield: 55%
Form: Hygroscopic powder
NMR (DMSO-d₆) δ:
11.80(1H, bs, NH)
9.30(3H, bs, NH₂, HCl)
8.00(1H, d, J=7Hz, C₆—H)
7.40(4H, s, C₆H₄Cl)
6.14(1H, t, J=6Hz, C₁'—H)
4.56(2H, s, CH₂C₆H₄Cl)
4.42–4.16(4H, m, C₃', ₄', ₅'—H)
3.83(1H, d, J=5Hz, CHCO)
2.43–2.08(3H, m, C₂'—H, (CH₃)₂CH—)
0.97, 0.93(each 3H, d, J=7Hz, CH₃)

Example 14

Str: R₂ = —CH₂—C₆H₄—Cl

R₁ = HCl.NH₂—CH—C(=O)—
       |
       CH₂
       |
       CH(CH₃)₂   (L)

Yield: 51%
Form: Hygroscopic powder
NMR (DMSO-d₆) δ:
11.80(1H, bs, N₃—H)
8.82(3H, bs, NH₂, HCl)
8.02(1H, d, J=7Hz, C₆—H)
7.41(4H, s, C₆H₄Cl)
6.14(1H, t, J=6Hz, C₁'—H)
4.57(2H, S, CH₂C₆H₄Cl)
4.41–4.20(4H, m, C₃', ₄', ₅'—H)
4.00–3.80(1H, m, CHCO)
2.53–2.32(m, C₂'—H, coalesced with DMSO)
1.85–1.67(3H, m, —CH₂CH(CH₃)₂)
0.86(6H, d, J=5Hz, CH₃ × 2)

Example 15

Str: R₂ = —CH₂—C₆H₄—Cl

R₁ = HCl.H-N(pyrrolidinyl)—C(=O)— (L)

Yield: 63%
Form: Hygroscopic powder
NMR (DMSO-d₆) δ:
11.86(1H, bs, NH)
9.99(2H, bs, proline NH, HCl)
8.03(1H, d, J=7Hz, C₆—H)
7.41(4H, s, C₆H₄Cl)
6.14(1H, t, J=6Hz, C₁'—H)
4.57(2H, s, CH₂C₆H₄Cl)
4.42–4.27(5H, m, C₃', ₄', ₅'—H, CHCO)
3.39–3.18(4H, m,
—NHCH₂CH₂CH₂)
2.40–2.32(2H, m, C₂'—H)
2.08–1.85(2H, m,
—NHCH₂CH₂CH₂)

Example 16

Str: R₂ = —CH₂—C₆H₄—Cl

R₁ = —C(=O)—CH₂CH₂NH₂·HCl

Yield: 61%
Form: Hygroscopic powder
NMR (DMSO-d₆) δ:
11.86(1H, bs, NH)
8.19(3H, bs, NH₂, HCl)
7.97(1H, d, J=7Hz, C₆—H)
7.41(4H, s, C₆H₄Cl)
6.12(1H, t, J=6Hz, C₁'—H)
4.55(2H, s, CH₂C₆H₄Cl)
4.31–4.18(4H, m, C₃', ₄', ₅'—H)
3.03(2H, t, J=6Hz, —CH₂CO)
2.77(2H, t, J=6Hz, NCH₂)
2.34(2H, t, J=5Hz, C₂'—H)

Example 17

Str: R₂ = —CH₂—C₆H₄—Cl

R₁ = —C(=O)—(piperidinyl)NH·HCl

Yield: 91%
Form: Hygroscopic powder
NMR (DMSO-d₆) δ:
11.86(1H, bs, NH)
9.22(2H, NH, NCl)
7.94(1H, d, J=7Hz, C₆—H)
7.41(4H, s, C₆H₄Cl)
6.12(1H, t, J=6Hz, C₁'—H)
4.54(2H, s, CH₂C₆H₄Cl)
4.28–4.16(4H, m, C₃', ₄', ₅'—H)
3.18–1.83(11H, m, C₂'—H, CO—(piperidine)—N—)

EXAMPLE 18

Preparation of 5'-O-benzyl-2'-deoxy-5-fluoro-3'-O-glycyluridine hydrochloride

To a solution of 1.00 g of 5'-O-benzyl-2'-deoxy-5-fluorouridine in 30 ml of anhydrous pyridine were added 0.78 g of N-(t-butoxycarbonyl)glycine and 1.80 g of 2,4,6-triisopropylbenzenesulfonyl chloride, and the mixture was subjected to reaction at room temperature overnight.

The reaction mixture was concentrated under reduced pressure, and the residue was distributed between ethyl acetate and water. The organic layer was washed with saturated aqueous solution of sodium hydrogen carbonate, dried over anhydrous magnesium sulfate and concentrated under reduced pressure. The residue was placed on silica gel column and eluted with 1% methanolchloroform for purification, giving 1.06 g of the desired 5'-O-benzyl-3'-O-[N-(t-butoxycarbonyl)glycyl]-2'-deoxy-5-fluorouridine.

Subsequently, the compound produced above (intermediate) was dissolved in 10 ml of 10% hydrochloric acid-dioxane and stirred for 2 hours at room temperature.

The reaction mixture was concentrated under reduced pressure, and the residue was placed on silica gel column, and eluted with 10% methanol-chloroform for purification, giving 0.77 g (60%) of the desired 5+-O-benzyl- 2'-deoxy-5-fluoro-3'-O-glycyluridine hydrochloride.

Form: Hygroscopic powder
NMR (DMSO-$d_6$) δ:
9.10 (3H, bs, $NH_2$, HCl), 7.97 (1H, d, J=7 Hz, $C_6$-H), 7.35 (5H, s, $C_6H_5$), 6.22 (1H, t, J=6 Hz, $C_{1'}$-H), 5.36 (1H, bs, $C_{3'}$-H), 4.58 (2H, s, C$\underline{H}_2$$C_6H_5$), 4.27 (1H, bs, $C_{4'}$-H), 3.81 (2H, s, $CH_2$CO), 3.77–3.71 (2H, m, $C_{5'}$-H), 2.55–2.31 ($C_{2'}$-H, coalesced with DMSO)

EXAMPLES 19–26

Following the procedure of Example 18 and using appropriate starting materials, the compounds shown below in Table 4 were prepared.

TABLE 4

Example 19

Str: $R_2$ = 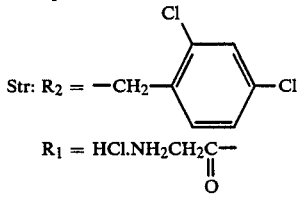

$R_1$ = HCl.NH$_2$CH$_2$C—
            ‖
            O

Yield: 67%
Form: Hygroscopic powder
NMR (DMSO-$d_6$)δ:
11.78(1H, bs, NH)
8.55(3H, bs, $NH_2$, HCl)
8.02(1H, d, J=7Hz, $C_6$—H)
7.62–7.41(3H, m, $C_6H_3Cl_2$)
6.16(1H, t, J=7Hz, $C_{1'}$—H)
4.61(2H, s, C$\underline{H}_2$$C_6H_3Cl_2$)
4.43–4.15(4H, m, $C_{3', 4', 5'}$—H)
3.83(2H, s, $CH_2$CO)
2.52–2.29($C_{2'}$—H, coalesced with DMSO)

Example 20

Str: $R_2$ = 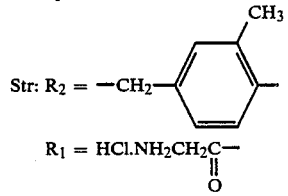

$R_1$ = HCl.NH$_2$CH$_2$C—
            ‖
            O

Yield: 80%
Form: Hygroscopic powder
NMR (DMSO-$d_6$)δ:
11.70(1H, bs, NH)
8.55(3H, bs, $NH_2$, HCl)
8.01(1H, d, J=7Hz, $C_6$—H)
7.28–7.11(4H, m, $C_6$$\underline{H}_4$$CH_3$)
6.13(1H, t, J=6Hz, $C_{1'}$—H)
4.51(2H, s, C$\underline{H}_2$—$C_6H_4$—$CH_3$)
4.40–4.19(4H, m, $C_{3', 4', 5'}$—H)
3.82(2H, s, $CH_2$CO)
2.46–2.31(5H, m, $C_{2'}$—H, —$C_6H_4$—C$\underline{H}_3$)

Example 21

TABLE 4-continued

Str: $R_2$ = 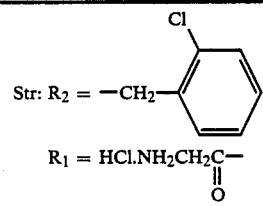

$R_1$ = HCl.NH$_2$CH$_2$C—
            ‖
            O

Yield: 9%
Form: Oil
NMR (DMSO-$d_6$)δ:
8.97(3H, bs, $NH_2$, HCl)
7.99(1H, d, J=7Hz, $C_6$—H)
7.61–7.29 (4H, m, $C_6H_4Cl$)
6.16(1H, t, J=6Hz, $C_{1'}$—H)
4.76–4.24(6H, m, C$\underline{H}_2$$C_6H_4Cl$, $C_{3', 4', 5'}$—H)
3.85(2H, s, $CH_2$CO)
2.54–2.33($C_{2'}$—H, coalesced with DMSO)

Example 22

Str: $R_2$ = 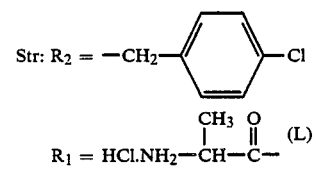

$CH_3$  O
            |    ‖
$R_1$ = HCl.NH$_2$—CH—C—    (L)

Yield: 17%
Form: Hygroscopic powder
NMR(DMSO-$d_6$)δ:
8.61(3H, bs, $NH_2$, HCl)
7.98(1H, d, J=7Hz, $C_6$—H)
7.40(4H, s, $C_6H_4Cl$)
6.14(1H, t, J=6Hz, $C_{1'}$—H)
4.55(2H, s, C$\underline{H}_2$$C_6H_4Cl$)
4.41–4.05(5H, m, $C_{3', 4', 5'}$—H, CH)
2.43–2.29(2H, m, $C_{2'}$—H)
1.42(3H, d, J=7Hz, $CH_3$)

Example 23

Str: $R_2$ = 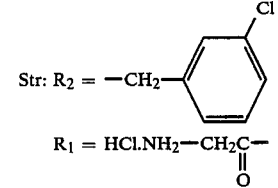

$R_1$ = HCl.NH$_2$—CH$_2$C—
              ‖
              O

Yield: 50%
Form: Hygroscopic powder
NMR(DMSO-$d_6$)δ:
9.01(3H, bs, $NH_2$, HCl)
8.01(1H, d, J=7Hz, $C_6$—H)
7.42–7.26(4H, m, $C_6H_4Cl$)
6.16(1H, t, J=6Hz, $C_{1'}$—H)
4.57(2H, s, C$\underline{H}_2$$C_6H_4Cl$)
4.41–4.15(4H, m, $C_{3', 4', 5'}$—H)
3.80(2H, s, $CH_2$CO)
2.54–2.31($C_{2'}$—H, coalesced with DMSO)

Example 24

Str: $R_2$ = 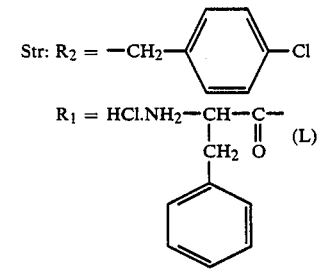

$R_1$ = HCl.NH$_2$—CH—C—
                |    ‖   (L)
               $CH_2$  O
                |

TABLE 4-continued

Yield: 19%
Form: Hygroscopic powder
NMR (DMSO-d$_6$)δ:
9.23(3H, bs, NH$_2$, HCl)
7.95(1H, d, J=7Hz, C$_6$—H)
7.40(4H, s, C$_6$H$_4$Cl)
7.26(5H, s, C$_6$H$_5$)
6.12(1H, t, J=7Hz, C$_{1'}$—H)
4.49(2H, s, CH$_2$C$_6$H$_4$Cl)
4.31-4.05(5H, m, C$_{3'}$, $_{4'}$, $_{5'}$—H, CH)
3.21-3.08(2H, m, CH$_2$C$_6$H$_5$)
2.29-2.19(2H, m, C$_{2'}$—H)

Example 25

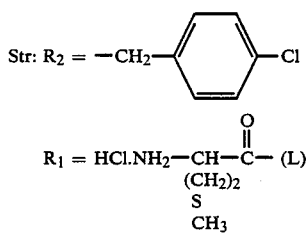

$R_1$ = HCl.NH$_2$—CH—C— (L)
         |           ‖
         (CH$_2$)$_2$   O
         |
         S
         |
         CH$_3$

Yield: 23%
Form: Hygroscopic powder
NMR(DMSO-d$_6$)δ:
11.78(1H, bs, NH)
8.78(3H, bs, NH$_2$, HCl)
8.01(1H, d, J=7Hz, C$_6$—H)
7.41(4H, s, C$_6$H$_4$Cl)
6.13(1H, t, J=6Hz, C$_{1'}$—H)
4.56(2H, s, CH$_2$C$_6$H$_4$Cl)
4.42-4.05(5H, m, C$_{3'}$, $_{4'}$, $_{5'}$—H CHCO)
2.66-2.02(9H, m, C$_{2'}$—H, CH$_3$—S—(CH$_2$)$_2$—)

Example 26

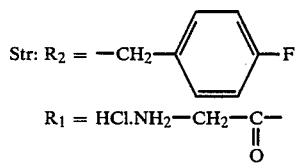

$R_1$ = HCl.NH$_2$—CH$_2$—C—
                        ‖
                        O

Yield: 72%
Form: Hygroscopic powder
NMR (DMSO-d$_6$)δ:
11.78(1H, bs, NH)
8.55(3H, bs, NH$_2$, HCl)
8.01(1H, d, J=7Hz, C$_6$—H)
7.50-7.08(4H, m, C$_6$H$_4$F)
6.13(1H, t, J=6Hz, C$_{1'}$—H)
4.54(2H, s, CH$_2$C$_6$H$_4$F)
4.41-4.14(4H, m, C$_{3'}$, $_{4'}$, $_{5'}$—H)
3.83(2H, s, CH$_2$CO)
2.46-2.28(2H, m, C$_{2'}$—H)

EXAMPLE 27

Preparation of 3'-O-(4-chlorobenzyl)-2'-deoxy-5'—O—(3-diethylaminopropanoyl)-5-fluorouridine hydrochloride To a solution of 3-diethylaminopropanoic acid hydrochloride in b 30 ml of tetrahydrofuran cooled to −15° C. were added 0.56 ml of triethylamine and 0.50 ml of isobutylchloroformate, giving mixed acid annydride.

To the mixture were added 1.00 g of 3'—O—(4-chlorobenzyl)-2'-deoxy-5-fluorouridine and 0.56 ml of triethylamine, and the mixture was stirred at room temperature overnight. The insoluble matter was filtered off and the filtrate was concentrated. The residue was placed on silica gel column and eluted with 5% methanolchloroform for purification, giving 0.10 g (7%) of 3'—O—(4-chlorobenzyl)-2'-deoxy-5'—O—(3-diethylaminopropanoyl)-5-fluorouridine hydrochloride.

Form : Hygroscopic powder
NMR (DMSO-d$_6$) δ:
11.96 (1H, bs, NH), 7.98 (1H, d, J=7Hz, C$_6$-H),
7.41 (4H, s, C$_6$H$_4$Cl), 6.16 (1H, t, J=6Hz, C$_{1'}$-H),
4.55 (2H, s, CH$_2$C$_6$H$_4$Cl),
4.27-4.23 (4H, m, C$_{3',4',5'}$-H),
3.19-2.94 (8H, m, CH$_2$CH$_2$CO, CH$_2$CH$_3$×2),
2.41-2.33 (2H, m, C$_{2'}$-H),
1.21 (6H, t, J=7Hz, CH$_3$×2)

EXAMPLE 28

Preparation of 3'-0-(4-chlorobenzyl)-2'-deoxy-5-fluoro-5'-O-glycyluridine L-tartrate To 0.50 g of 5'-O-[N-(t-butoxycarbonyl)glycyl]-3'-O-(4-chlorobenzyl)-2'-deoxy-5-fluorouridine obtained in Example 8 (A) was added 2 ml of 4N-hydrochloric aciddioxane, and the mixture was left to stand for 15 minutes at room temperature. Subsequently the solvent was evaporated and the residue was dissolved in a small amount of water. The solution was made weakly basic with saturated aqueous solution of sodium hydrogen carbonate and extracted three times with 40 ml of ethyl acetate. The ethyl acetate layer was dried over anhydrous magnesium sulfate and a solution of 0.14 g of L-tartaric acid in ethyl acetate was added thereto and the mixture was concentrated to about 40 ml. The precipitate thus formed was filtered, giving 0.38 g (65%) of 3'—O—(4-chloro-benzyl)-2'-deoxy-5-fluoro-5'-0-glycyluridine L-tartrate.

Form : Hygroscopic powder
NMR (DMSO-d$_6$) δ:
7.97 (1H, d, J=7Hz, C$_6$-H), 7.40 (4H, s, C$_6$H$_4$Cl),
7.26 (7H, bs, NH, NH$_2$, OH×2, COOH×2),
6.14 (1H, t, J=6Hz, C$_1'$-H), 4.54 (2H, s, CH$_2$C$_6$H$_4$Cl),
4.43-4.20 (4H, m, C$_{3',4',5'}$-H),
4.06 (2H, s, HOOCCHOHCHOHCOOH), 3.75 (2H, s, CH$_2$CO), 2.41-2.28 (2H, m, C$_{2'}$-H)

EXAMPLES 29 and 30

Following the procedure of Example 28 and using appropriate starting materials, the compounds shown in Table 5 were prepared.

TABLE 5

Example 29

Str:

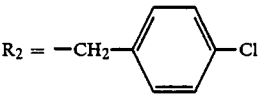

$R_1$ = HOOCCH=CHCOOH.NH$_2$—CH$_2$—C—
                                          ‖
                                          O

Yield: 65%
Form: Hygroscopic powder
NMR (DMSO-d$_6$) δ:
7.98 (1H, d, J=7Hz, C$_6$—H)
7.74 (5H, bs, NH, NH$_2$, COOH × 2)
7.40 (4H, s, C$_6$H$_4$Cl)
6.52 (2H, s, HOOCCH=CHCOOH)
6.14 (1H, t, J=7Hz, C$_{1'}$—H)
4.54 (2H, s, CH$_2$C$_6$H$_4$Cl)
4.38-4.18 (4H, m, C$_{3',4',5'}$—H)
3.64 (2H, s, CH$_2$CO)
2.40-2.28 (2H, m, C$_{2'}$—H)

Example 30

TABLE 5-continued

Str:

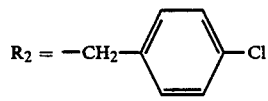

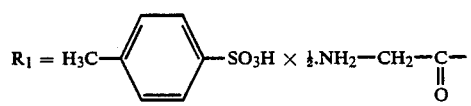

Yield: 58%
Form: Hygroscopic powder
NMR (DMSO-$d_6$) δ:
8.30 (2.5H, bs, $NH_2$ and $SO_3H \times \frac{1}{2}$)
7.98 (1H, d, J=7Hz, $C_6$—H)
7.49 (1H, d, J=8Hz, p-tosylate $C_{2,6}$—H $\times \frac{1}{2}$)
7.40 (4H, s, $C_6H_4Cl$)
7.11 (1H, d, J=8Hz, p-tosylate $C_{3,5}$—H $\times \frac{1}{2}$)
6.24–6.08 (1H, m, $C_{1'}$—H)
4.54 (2H, s, $CH_2C_6H_4Cl$)
4.42–4.38 (2H, m, $C_{3'4'}$—H)
4.23–4.20 (2H, m, $C_{5'}$—H)
3.87 (2H, s, —$CH_2CO$)
2.42–2.28 (3.5H, m, $C_{2'}$—H and $CH_3 \times \frac{1}{2}$)

Pharmacological Test I

The compound 12 of the invention was tested for antitumor effect to prove the usefulness of the compound.

Test Methods (a) Method of determining the antitumor activity

Tissues of Sarcoma-180 were subcutaneously transplanted into the back of male mice of ICR/JCL strain (weighing 27 to 30 g) in an amount of $5 \times 10^6$ cells each. The test compound was administered in the form of a weakly acidic aqueous solution. The solution was orally given to each mouse (7 mice in each group) in a dose of 1.0 ml/100 g body weight once a day for 7 consecutive days starting 24 hours after the transplantation, and a weakly acidic aqueous solution containing no test compound was orally administered to the control group in an amount of 1.0 ml/100 g body weight once a day for 7 consecutive days starting 24 hours after the transplantation.

The tumor was removed from the body on the 10the day after the transplantation and weighed to calculate the average weight of the tumors in the group to which the test compound-containing solution was given and the corresponding weight in the control group. The effective dose ($ED_{50}$) for achieving 50% cancer inhibition was determined from the dose-response curve. The dose of 50% inhibition of body weight gain ($IB_{50}$) was determined from the dose-body weight change curve. The therapeutic index (T.I. = $IB_{50}/ED_{50}$) was determined with the results shown below in Table 6.

TABLE 6

| | $ED_{50}$ (mg/kg/day) | $IB_{50}$ (mg/kg/day) | T.I. |
|---|---|---|---|
| Compound 12 | 0.75 | 3.60 | 4.80 |
| $O^{3'}$-p-chlorobenzyl-2'-deoxy-5-fluorouridine | 0.94 | 1.54 | 1.64 |

Table 6 shows that compound 12 is higher in efficacy and greater in therapeutic index than $O^{3'}$-p-chlorobenzyl-2'-deoxy-5-fluorouridine, hence superior in anti-cancer effect.

Pharmacological Test II

Sarcoma-180 subcultured in ascites of ICR mice was diluted with a physiological saline and subcutaneously transplanted into the backs of ICR mice in an amount of $2 \times 10^7$ cells each. Twenty-four hours after the transplantation, a test compound dissolved in sterilized physiological saline was administered to the tail vein of each of the mice once a day for 7 consecutive days.

The solid tumor was isolated from under the dorsal skin of mice on the 10th day after the transplantation to measure the weight of the tumor. There was determined the ratio (T/C) of the weight of tumor (T) of the test compound group to the weight of tumor (C) of the control group. The 50% tumor inhibition dose ($ED_{50}$ value) in which T/C is 0.5 was determined from the dose response curve of dosage and the ratio (T/C). Table 7 shows the results.

TABLE 7

| Ex. No. | Test Compound <Formula (I)> $R_2$ | $R_1$ | $ED_{50}$ (mg/kg) |
|---|---|---|---|
| 8 (E) | —$CH_2$—⟨C₆H₄⟩—Cl | $HCl.NH_2CH_2$—C(=O)— | 1.0 |
| 13 | —$CH_2$—⟨C₆H₄⟩—Cl | $HCl.NH_2CH$—C(=O)—, CH(CH$_3$)(CH$_3$) | 1.5 |
| 14 | —$CH_2$—⟨C₆H₄⟩—Cl | $HCl.NH_2CH$—C(=O)—, $CH_2$—CH(CH$_3$)(CH$_3$) | 1.5 |

TABLE 7-continued

| Ex. No. | Test Compound <Formula (I)> R₂ | R₁ | ED₅₀ (mg/kg) |
|---|---|---|---|
| 19 | —CH₂—(C₆H₃)(Cl)(Cl) | HCl.NH₂CH₂—C(=O)— | 0.8 |
| 22 | —CH₂—(C₆H₄)—Cl | HCl.NH₂CH(CH₃)—C(=O)— | 1.0 |
| 28 | —CH₂—(C₆H₄)—Cl | HO—CH(COOH)—CH(OH)—COOH.NH₂CH₂—C(=O)— | 1.0 |

Given below are Preparation Examples illustrating the preparation of pharmaceutical compositions containing the compound of the invention.

PREPARATION EXAMPLE 1

Preparation of encapsulated composition Compound 3, lactose, crystalline cellulose and corn starch were mixed together in the following proportions. Magnesium stearate was added in the amount shown below, and the mixture was encapsulated in an amount of about 293 mg per capsule with use of a suitable encapsulating device.

| Components | mg/capsule |
|---|---|
| Compound 3 | 200.0 |
| Lactose | 30.0 |
| Crystalline cellulose | 50.0 |
| Corn starch | 10.0 |
| Magnesium stearate | 3.0 |
| | 293.0 |

PREPARATION EXAMPLE 2

Preparation of granulated composition Compound 7, lactose, crystalline cellulose and corn starch were mixed together in the following proportions. A 10% solution of hydroxypropyl cellulose in ethanol was added and the mixture was kneaded and granulated with use of an adequate granulation device. The granules were dried and regulated to a size of 12 to 42 meshes. The resulting granules were coated with hydroxypropylmethyl cellulose in the amount shown below with use of a suitable coater and regulated to a size of 12 to 42 meshes.

| Components | mg/capsule |
|---|---|
| Compound 7 | 200.0 |
| Lactose | 200.0 |
| Crystalline cellulose | 311.0 |
| Corn starch | 200.0 |
| Hydroxypropyl cellulose | 10.0 |
| Hydroxypropylmethyl cellulose | 70.0 |
| Fatty acid monoglyceride | 3.5 |
| Titanium dioxide | 5.5 |
| | 1,000.0 |

PREPARATION EXAMPLE 3

Preparation of tabletted composition

Compound 1, corn starch and cellulose calcium glycolate were mixed together in the following proportions. A 10% solution of hydroxypropyl cellulose in ethanol was added after which the mixture was kneaded and granulated with an adequate granulation device. The granules were dried and the following proportions of magnesium stearate and silicic acid anhydride were added. The mixture was formed into tablets with use of an adequate tablet-forming device, and the tablets were coated with hydroxypropylmethyl cellulose.

| Components | mg/capsule |
|---|---|
| Compound 1 | 200.0 |
| Corn starch | 5.0 |
| Cellulose calcium glycolate | 20.0 |
| Hydroxypropyl cellulose | 2.0 |
| Magnesium stearate | 2.5 |
| Silicic acid anhydride | 2.5 |
| Hydroxypropylmethyl cellulose | 19.999 |
| Macrogol 6000 | 0.001 |
| Titanium dioxide | 2.0 |
| | 254 |

PREPARATION EXAMPLE 4

Preparation of composition in suppository form

"Witepsol W-35" (trademark, product of Dynamite Nobel Co., Ltd., West Germany) was fused at about 60° C. and the solution was maintained at about 45° C. The solution and the compound 5 was mixed in the following proportions and shaped into a suppository form weighting 1 g each with use of a suitable suppository-forming device.

| Components | mg/suppository |
|---|---|
| Compound 5 | 400.0 |
| Witepsol W-35 | 600.0 |
| | 1,000.0 |

| Preparation Example 5 | |
|---|---|
| Compound of Example 13 | 50 mg |
| Lactose | 97 mg |
| Crystalline cellulose | 50 mg |

-continued
Preparation Example 5

| | |
|---|---|
| Magnesium stearate | 3 mg |

Capsules (200 mg each) were prepared which each had the foregoing composition.

Preparation Example 6

| | |
|---|---|
| Compound of Example 14 | 10 mg |
| Lactose | 184 mg |
| Crystalline cellulose | 100 mg |
| Magnesium stearate | 6 mg |

Capsules (300 mg each) were prepared which each had the foregoing composition.

Preparation Example 7

| | |
|---|---|
| Compound of Example 19 | 10 mg |
| Lactose | 240 mg |
| Corn starch | 340 mg |
| Hydroxypropyl cellulose | 10 mg |

Granules (600 mg each wrapper) were prepared which each had the foregoing composition.

Preparation Example 8

| | |
|---|---|
| Compound of Example 8 (E) | 10 mg |
| Macrogol 300 | 500 mg |
| Distilled water for injection | (appropriately) |

An injection solution (5 ml per ampul) was prepared which had the foregoing composition.

PREPARATION EXAMPLE 9

A thousand tablets for oral administration were prepared which each contained 10 mg of the compound obtained in Example 22 and which each had the following composition.

| | |
|---|---|
| Compound of Example 22 | 10 g |
| Lactose (Japanese Pharmacopeia) | 45 g |
| Corn starch (Japanese Pharmacopeia) | 25 g |
| Crytalline cellulose (Japanese Pharmacopeia) | 25 g |
| Methyl cellulose (Japanese Pharmacopeia) | 1.5 g |
| Magnesium stearate (Japanese Pharmacopeia) | 1 g |

The compound of Example 22, lactose, corn starch and crystalline cellulose were thoroughly mixed and the mixture was granulated with a 5% aqueous solution of methyl cellulose. The granules thus obtained were passed through a 200-mesh sieve and carefully dried. The dry granules were passed through a 200-mesh sieve and mixed with magnesium stearate. The mixture was pressed into

Preparation Example 10

| | |
|---|---|
| Compound of Example 9 | 10 mg |
| Macrogol 300 | 500 mg |
| Distilled water for injection | adequate amount |

An injection solution (5 ml per ampul) was prepared which had the foregoing composition.

Preparation Example 11

| | |
|---|---|
| Compound of Example 8 (E) | 0.4 g |
| Polyethylene glycol 1000 | 30 g |
| Polyethylene glycol 6000 | 50 g |
| Purified water | 20 g |

Suppositories weighting 2.5 g each were prepared which each had the above composition. The tumors which can be treated with the 2,-deoxy-5-fluorouridine derivatives, and salts thereof, of the present invention are the tumors which are susceptible to therapy by FudR.

We claim:

1. A 2'-deoxy-5-fluorouridine derivative represented by the formula $$\begin{array}{c}\text{structure (I)}\end{array}$$

wherein:
one of $R_1$ and $R_2$ is a benzyl group which may have 1, 2 or 3 substituents selected from the group consisting of $C_1$-$C_6$ alkyl group, $C_1$-$C_6$ alkoxy group, $C_1$-$C_3$ halogenated alkyl group, halogen atom, hydroxyl group and nitro group on the phenyl ring, and the other constitutes an amino acid residue having 2 to 20 carbon atoms, or a salt thereof.

2. A compound according to claim 1 and a salt thereof in which the benzyl group which may have substituent is one member selected from the group consisting of benzyl, 2-chlorobenzyl, 3-chlorobenzyl, 4-chlorobenzyl, 2-bromobenzyl, 3-bromobenzyl, 4-bromobenzyl, 2-fluorobenzyl, 3- fluorobenzyl, 4-fluorobenzyl, 2,4-dichlorobenzyl, 3,4-dichlorobenzyl, 2-chloro-4-chloro-4-bromo-benzyl, 2-trifluoromethylbenzyl, 4-trifluoromethylbenzyl, 4-nitrobenzyl, 2,4-dinitrobenzyl, 2methylbenzyl, 4-methylbenzyl, 4-ethylbenzyl-4-tert-butylbenzyl-4methoxybenzyl, 3-ethoxybenzyl, 4-hydroxybenzyl, 2,4dihydroxybenzyl and 2-methyl-3-nitrobenzyl.

3. A compound according to claim 1 in which the benzyl group which may have substituent is benzyl group having 1 or 2 halogen atoms on the phenyl ring.

4. A compound according to claim 1 in which the amino acid residue is α-amino acid residue.

5. A compound according to claim 2 in which the α-amino acid residue is a residue of an amino acid which is a protein constituent.

6. A compound according to claim 5 in which the amino acid residue as the protein constituent is a residue of the amino acid selected from the group consisting of alanine, isoleucine, glycine, serine, threonine, valine, leucine, arginine, hydroxylysine, lysine, asparagine, cysteine, methionine, tyrosine, phenylalanine, tryptophan, histidine, hydroxyproline and proline.

7. A compound according to claim 1 in which the amino acid residue is a residue of a member selected from the group consisting of alanine, isoleucine, glycine, O-acetylserine, valine, leucine, lysine, aspartic acid-$\beta$-benzyl ester, phenylalanine, histidine and proline.

8. A compound according to claim 2 in which $R_1$ is an $\alpha$-amino acid residue and $R_2$ is one member selected from the group consisting of benzyl, 2-chlorobenzyl, 3chlorobenzyl, 4-chlorobenzyl, 2-bromobenzyl, 3-bromobenzyl, 4-bromobenzyl, 2-fluorobenzyl, 3-fluorobenzyl, 4-fluorobenzyl, 2,4-dichlorobenzyl, 3,4-dichlorobenzyl, 2- chloro-4-bromobenzyl, 2-trifluoromethylbenzyl, 4-trifluoromethylbenzyl, 4-nitrobenzyl, 2,4-dinitrobenzyl, 2-methylbenzyl, 4-methylbenzyl, 4-ethylbenzyl, 4-tertbutylbenzyl, 4-methoxybenzyl, 3-ethoxybenzyl, 4hydroxybenzyl, 2,4-dihydroxybenzyl and 2-methyl-3nitrobenzyl.

9. A compound according to claim 3 in which $R_1$ is an $\alpha$-amino acid residue and $R_2$ is a benzyl group having 1 or 2 halogen atoms on the phenyl ring.

10. A compound according to claim 2 in which $R_1$ is a residue of an amino acid which is a protein constituent and $R_2$ is one member selected from the group consisting of benzyl, 2-chlorobenzyl, 3-chlorobenzyl, 4-chlorobenzyl, 2-bromobenzyl, 3-bromobenzyl, 4-bromobenzyl, 2-fluorobenzyl, 3-fluorobenzyl, 4-fluorobenzyl, 2,4-dichlorobenzyl, 3,4-dichlorobenzyl, 2-chloro-4-bromobenzyl, 2-trifluoromethylbenzyl, 4-trifluoromethylbenzyl, 4-nitrobenzyl, 2,4-dinitrobenzyl, 2-methylbenzyl, 4-methylbenzyl, 4-ethylbenzyl, 4-tert-butylbenzyl, 4-methoxybenzyl, 3-ethoxybenzyl, 4-hydroxybenzyl, 2,4-dihydroxybenzyl and 2-methyl-3-nitrobenzyl.

11. A compound according to claim 3 in which $R_1$ is a residue of an amino acid which is a protein constituent and $R_2$ is a benzyl group having 1 to 2 halogen atoms on the phenyl ring.

12. A compound according to claim 10 in which $R_1$ is a residue of the amino acid selected from the group consisting of alanine, isoleucine, glycine, serine, threonine, valine, leucine, arginine, hydroxylysine, lysine, asparagine, aspartic acid, glutamine, glutamic acid, cystine, cysteine, methionine, tyrosine, phenylalanine, tryptophan, histidine, hydroxyproline and proline.

13. A compound according to claim 11 in which $R_1$ is a residue of the amino acid selected from the group consisting of alanine, isoleucine, glycine, serine, threonine, valine, leucine, arginine, hydroxylysine, lysine, asparagine, aspartic acid, glutamine, glutamic acid, cystine, cysteine, methionine, tyrosine, phenylalanine, tryptophan, histidine, hydroxyproline and proline.

14. A compound according to claim 2 in which $R_1$ is a residue of a member selected from the group consisting of alanine, isoleucine, glycine, O-acetylserine, valine, leucine, lysine, aspartic acid-$\beta$-benzyl ester, phenylalanine, histidine and proline and $R_2$ is one member selected from the group consisting of benzyl, 2-chlorobenzyl, 3-chlorobenzyl, 4-chlorobenzyl, 2-bromobenzyl, 3-bromobenzyl, 4-bromobenzyl, 2-fluorobenzyl, 3-fluorobenzyl, 4-fluorobenzyl, 2,4-dichlorobenzyl, 3,4dichlorobenzyl, 2-chloro-4-bromobenzyl, 2-trifluoromethylbenzyl, 4-trifluoromethylbenzyl, 4-nitrobenzyl, 2,4-dinitrobenzyl, 2-methylbenzyl, 4-methylbenzyl, 4ethylbenzyl, .4-tert-butylbenzyl, 4-methoxybenzyl, 3-ethoxybenzyl, 4-hydroxybenzyl, 2,4-dihydroxybenzyl and 2-methyl-3-nitrobenzyl.

15. A compound according to claim 3 in which $R_1$ is a residue of a member selected from the group consisting of alanine, isoleucine, glycine, 0-acetylserine, valine, leucine, lysine, aspartic acid-$\beta$-benzyl ester, phenylalanine, histidine and proline and $R_2$ is a benzyl group having 1 or 2 halogen atoms on the phenyl ring.

16. A compound according to claim 1 in which one of $R_1$ and $R_2$ is a benzyl group which may have 1 to 3 substituents selected from the group consisting of lower alkyl group, lower alkoxy group and halogen atom on the phenyl ring, and the other of $R_1$ and $R_2$ is a group represented by the formula

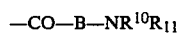

wherein B is a lower alkylene group which may have a phenyl or lower alkylthio group, and $R^{10}$ and $R_{11}$ each represent a hydrogen atom or lower alkyl group or taken together with a nitrogen atom to which they are attached and form piperidine ring, or a pyrrolidinylcarbonyl or piperidylcarbonyl group in which the carbonyl group is not attached to the nitrogen atom in the hetero ring.

17. A compound according to claim 16 in which $R_2$ is a benzyl group which may have 1 to 3 substituents selected from the group consisting of lower alkyl group, lower alkoxy group and halogen atom on the phenyl ring.

18. A compound according to claim 17 in which $R_1$ is a group represented by the formula

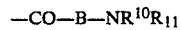

wherein $R^{10}$ and $R_1$ each represent hydrogen atom and B is an unsubstituted lower alkylene group, and $R_2$ is a benzyl group which has 1 or 2 halogen atoms on the phenyl ring.

19. A compound according to claim 17 in which $R_1$ is a group represented by the formula

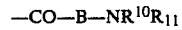

wherein $R^{10}$ and $R_{11}$ each represent hydrogen atom and B is a lower alkylene group which has a phenyl or lower alkylthio group as the substituent end $R_2$ is a benzyl group which has 1 or 2 halogen atoms on the phenyl ring.

20. A compound according to claim 1 which is 3'-O-(4-chlorobenzyl)-2'-deoxy-5-fluoro-5'-O-glycyluridine hydrochloride.

21. A compound according to claim 1 which is 3'-O-(2,4-dichlorobenzyl)-2'-deoxy-5-fluoro-5'-O-glycyluridine hydrochloride.

22. A compound according to claim 1 which is 3'-O-(4-chlorobenzyl)-2'-deoxy-5-fluoro-5'-O-valyluridine hydrochloride.

* * * * *